(12) United States Patent
Kamon

(10) Patent No.: US 12,362,061 B2
(45) Date of Patent: Jul. 15, 2025

(54) MEDICAL IMAGE PROCESSING DEVICE, PROCESSOR DEVICE, ENDOSCOPE SYSTEM, MEDICAL IMAGE PROCESSING METHOD, AND PROGRAM

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 762 days.

(21) Appl. No.: 17/008,650

(22) Filed: Sep. 1, 2020

(65) Prior Publication Data
US 2021/0082568 A1 Mar. 18, 2021

(30) Foreign Application Priority Data
Sep. 18, 2019 (JP) ................................ 2019-169600

(51) Int. Cl.
*G16H 30/40* (2018.01)
*A61B 1/00* (2006.01)
(Continued)

(52) U.S. Cl.
CPC ......... *G16H 30/40* (2018.01); *A61B 1/00006* (2013.01); *A61B 1/000096* (2022.02);
(Continued)

(58) Field of Classification Search
CPC ........ G16H 20/40; G16H 30/40; G16H 40/63; G16H 50/20; A61B 1/00006;
(Continued)

(56) References Cited

U.S. PATENT DOCUMENTS 6,944,330 B2 9/2005 Novak et al.
8,600,134 B2 * 12/2013 Vercauteren .............. G06T 5/50
382/128
(Continued)

FOREIGN PATENT DOCUMENTS

JP H10323326 12/1998
JP 2004531315 10/2004
(Continued)

OTHER PUBLICATIONS

"Office Action of Japan Counterpart Application" with English translation thereof, issued on Jun. 17, 2022, p. 1-p. 8.
(Continued)

*Primary Examiner* — Nay A Maung
*Assistant Examiner* — Jose M Torres
(74) *Attorney, Agent, or Firm* — JCIPRNET

(57) ABSTRACT

Provided is a medical image processing device, a processor device, a medical image processing method, and a computer-readable medium capable of obtaining a recognition result related to a region of interest and storing and displaying a medical image in which the recognition result matches an intention of an operator.

The medical image processing device includes an image acquisition unit (40) that acquires a medical image (38), an acquired image storage unit (46A) that stores the acquired medical image, a recognition processing unit (42A) that performs recognition processing on the acquired medical image, a user input signal acquisition unit (50) that acquires a user input signal transmitted according to an operation of a user, and a selection unit (48) that selects a medical image from medical images for which a result of the recognition processing related to a region of interest is obtained in a case where the user input signal is acquired.

19 Claims, 12 Drawing Sheets

(51) Int. Cl.
G06T 7/00 (2017.01)
G06T 7/11 (2017.01)
G06V 10/44 (2022.01)
G06V 10/82 (2022.01)

(52) U.S. Cl.
CPC ........ *A61B 1/0004* (2022.02); *A61B 1/00042* (2022.02); *G06T 7/0012* (2013.01); *G06T 7/11* (2017.01); *G06V 10/454* (2022.01); *G06V 10/82* (2022.01); *A61B 1/000094* (2022.02); *G06T 2207/30004* (2013.01); *G06T 2207/30168* (2013.01)

(58) Field of Classification Search
CPC ........ A61B 1/000094; A61B 1/000096; A61B 1/0004; A61B 1/00042; A61B 1/043; A61B 1/0638; G06T 7/0012; G06T 7/11; G06T 2207/30004; G06T 2207/30168; G06V 10/454; G06V 10/82; G06V 2201/032
See application file for complete search history.

(56) References Cited

U.S. PATENT DOCUMENTS

| | | | |
|---|---|---|---|
| 10,223,785 | B2 | 3/2019 | Kitamura et al. |
| 10,776,921 | B2 | 9/2020 | Kitamura et al. |
| 11,103,197 | B2 | 8/2021 | Kamon |
| 2009/0105544 | A1 | 4/2009 | Takahira |
| 2011/0152687 | A1* | 6/2011 | Iimura ................... A61B 8/485 600/443 |
| 2012/0113239 | A1 | 5/2012 | Krupnik et al. |
| 2012/0220840 | A1* | 8/2012 | Morita ................. A61B 1/0638 600/109 |
| 2013/0152020 | A1* | 6/2013 | Nishiyama ............. G16H 30/20 715/835 |
| 2015/0320299 | A1* | 11/2015 | Krupnik ........... A61B 1/000094 348/65 |
| 2016/0128545 | A1* | 5/2016 | Morita ................. A61B 1/0005 600/109 |
| 2016/0379363 | A1* | 12/2016 | Kitamura .............. G06T 7/0012 600/371 |
| 2017/0004625 | A1* | 1/2017 | Kamiyama ........... G06T 7/0016 |
| 2017/0098301 | A1* | 4/2017 | Ikemoto ................ G06T 7/0012 |
| 2018/0098690 | A1* | 4/2018 | Iwaki ....................... A61B 1/05 |
| 2019/0008361 | A1* | 1/2019 | Imai ................... A61B 1/00055 |
| 2019/0239718 | A1* | 8/2019 | Iwaki .................... G06T 7/0012 |
| 2020/0065970 | A1* | 2/2020 | Sonoda ............ A61B 1/000094 |
| 2020/0090333 | A1* | 3/2020 | Iwaki ........................ G06T 7/70 |
| 2020/0193602 | A1 | 6/2020 | Kamon |
| 2021/0161363 | A1* | 6/2021 | Makino ..................... G06T 7/00 |
| 2021/0174115 | A1* | 6/2021 | Kamon ................ G06F 18/213 |
| 2021/0209398 | A1* | 7/2021 | Endo .................... G06T 7/0012 |
| 2021/0361142 | A1* | 11/2021 | Kitamura ............... A61B 5/749 |

FOREIGN PATENT DOCUMENTS

| | | |
|---|---|---|
| JP | 2009100935 | 5/2009 |
| JP | 2012239757 | 12/2012 |
| JP | 2013222383 | 10/2013 |
| JP | 2014220690 | 11/2014 |
| JP | 2015173827 | 10/2015 |
| WO | 2016199273 | 12/2016 |
| WO | 2017199408 | 11/2017 |
| WO | 2019039259 | 2/2019 |
| WO | 2019049503 | 3/2019 |
| WO | 2019123986 | 6/2019 |

OTHER PUBLICATIONS

Office Action of Japan Counterpart Application, with English translation thereof, issued on Sep. 5, 2022, pp. 1-11.
Office Action of Japan Counterpart Application, with English translation thereof, issued on Jul. 19, 2023, pp. 1-6.

* cited by examiner

MEDICAL IMAGE PROCESSING DEVICE, PROCESSOR DEVICE, ENDOSCOPE SYSTEM, MEDICAL IMAGE PROCESSING METHOD, AND PROGRAM

CROSS-REFERENCE TO RELATED APPLICATIONS

The present application claims priority under 35 U.S.C. § 119 to Japanese Patent Application No. 2019-169600 filed on Sep. 18, 2019. The above application is hereby expressly incorporated by reference, in its entirety, into the present application.

BACKGROUND OF THE INVENTION

1. Field of the Invention

The present invention relates to a medical image processing device, a processor device, an endoscope system, a medical image processing method, and a program.

2. Description of the Related Art

A system that introduces AI technology or the like into an endoscopic image A system that introduces an AI technology or the like to an endoscopic image or the like to detect a lesion and support diagnosis is attracting attention because it reduces an oversight rate of a lesion and leads to a reduction of unnecessary biopsies. Such a system operates in real time during execution of an endoscopy, and implements a notification to the doctor such as performing a screen display of a recognition result and the like. AI is an abbreviation for Artificial Intelligence.

JP2012-239757A discloses an endoscope device that generates a normal light observation image captured by using an illumination for normal light observation and a special light observation image captured by using an illumination for special light observation. In a case where a freeze button is pressed in a display mode for simultaneously displaying the normal light observation image and the special light observation image, the device disclosed in the same document simultaneously displays a still image of the normal light observation image and a still image of the special light observation image.

At this time, the device calculates an amount of movement of two consecutive frames of each of the normal light observation image and the special light observation image for a certain period from an input of a freeze command signal and updates an image in a freeze memory in a case where the amount of movement is minimized. The device displays the image stored in the freeze memory at a timing at which a certain period has elapsed. This implements the display of a still image with no shake or little shake.

SUMMARY OF THE INVENTION

However, in an actual endoscopy, there may be a case where it is difficult for a doctor to check a result of recognition processing because the observation image greatly varies due to the influence of body motion or the like and the result of the recognition processing is not obtained stably. On the other hand, the doctor can check the observation image and the result of the recognition processing by performing a freeze command operation or the like during the endoscopy. However, there is a problem that it is difficult to perform a freeze command operation at an appropriate timing and obtain an observation image intended by an operator. Examples of a case where it is difficult to acquire a still image intended by the operator on the basis of the freeze command operation include a case where a region of interest cannot be detected over several frames and a case where a disease type or the like of the region of interest cannot be classified and it is determined that classification is impossible.

In endoscopy, a result of the recognition processing is not always obtained stably for two consecutive frames. In this case, the device disclosed in JP2012-239757A displays an image in which entire movement of the normal light observation image and entire movement of the special light image are minimized, and even in the case where the image is the image in which the entire movement of the normal light observation image and the like is minimized, the result of the recognition processing may not be obtained.

The above-described problems in the endoscopy are similarly present in devices that perform imaging of medical images other than endoscope systems such as a CT device.

The present invention has been made in view of such circumstances, and an object of the present invention is to provide a medical image processing device, a processor device, medical image processing method, and program capable of obtaining a recognition result related to a region of interest and storing and displaying a medical image in which the recognition result matches an intention of an operator.

To achieve the above object, the following aspects of the invention are provided.

A medical image processing device according to a first aspect is a medical image processing device comprising an image acquisition unit that acquires a medical image; an acquired image storage unit that stores the medical image acquired by using the image acquisition unit; a recognition processing unit that performs recognition processing on the medical image acquired by using the image acquisition unit; a user input signal acquisition unit that acquires a user input signal transmitted according to an operation of a user; and a selection unit that selects a medical image from medical images for which a result of the recognition processing related to a region of interest is obtained in the recognition processing performed by using the recognition processing unit in a case where the user input signal is acquired.

According to the first aspect, a medical image is selected from the medical images for which the result of the recognition processing related to the region of interest is obtained. As a result, the selection unit can obtain the recognition result and can select a medical image in which the recognition result matches an intention of an operator.

The medical image may be a moving image or a still image group including a plurality of still images. An endoscopic image is included as an example of a medical image.

The medical image may be acquired from an imaging device that generates the medical image, or may be acquired from a storage device that stores the medical image acquired by using the imaging device.

A region of interest of the medical image represents a region in which a feature quantity based on the pixel value or the like is distinguished from a peripheral region.

As a medical image to be selected by the selection unit, one medical image updated on the basis of the recognition result of the recognition processing unit can be applied. As the medical image to be selected by the selection unit, a plurality of medical images for which the recognition result of the recognition processing unit is obtained can be applied.

According to a second aspect, in the medical image processing device according to the first aspect, the selection unit may be configured to select a medical image from medical images that is acquired by using the image acquisition unit at a timing near a timing at which the user input signal is acquired and for which the result of the recognition processing related to the region of interest is obtained.

According to the second aspect, the selection unit can select the medical image at the timing near the acquisition timing of the user input signal.

The timing near the acquisition timing of the user input signal may be before the acquisition timing of the user input signal or after the acquisition timing of the user input signal. The timing near the acquisition timing of the user input signal may be the acquisition timing of the user input signal.

The nearness can be prescribed according to an acquisition cycle of the medical image, a recognition result of the medical image, and the like.

According to a third aspect, in the medical image processing device according to the first or second aspect, the medical image processing device may be configured to comprise a display unit that displays the medical image selected by using the selection unit, in which the display unit displays the medical image selected by using the selection unit for a certain period from the timing at which the user input signal is acquired.

According to the third aspect, in a case where the user input signal for displaying the still image of the medical image is acquired, the display unit can display the medical image selected by using the selection unit for a certain period.

The certain period can be prescribed according to the acquisition cycle of the medical image, the recognition result of the medical image, and the like.

According to a fourth aspect, in the medical image processing device according to the third aspect, the medical image processing device may be configured to comprise a processing unit that performs processing on a medical image to be processed according to a recognition result of the medical image using the recognition processing unit, in which the display unit displays the medical image on which processing is performed by using the processing unit.

According to the fourth aspect, the display unit can display the medical image that is subjected to the prescribed processing by using the processing unit.

As an example of the processing, emphasis processing of the region of interest can be included. Examples of the emphasis processing include a superimposed display of a closed curve surrounding at least a portion of the region of interest, a superimposed display of an arrow indicating the region of interest to be processed, and a superimposed display of a figure at four corners of the region of interest.

The display unit may display the processing result of the processing using the processing unit.

According to a fifth aspect, in the medical image processing device according to any one of the first to third aspects, the medical image processing device may be configured to comprise a selected image storage unit that stores the medical image selected by using the selection unit.

According to the fifth aspect, the selected image storage unit can store the selected medical image.

According to a sixth aspect, in the medical image processing device according to the fifth aspect, the selected image storage unit may be configured to store the medical image to be stored in association with a result of the recognition processing of the medical image to be stored.

According to the sixth aspect, the selected image storage unit can store the selected medical image in association with the result of the recognition processing for the selected medical image.

According to a seventh aspect, in the medical image processing device according to the fifth or sixth aspect, the medical image processing device may be configured to comprise a processing unit that performs processing on a medical image to be processed according to a recognition result of the medical image using the recognition processing unit, in which the selected image storage unit stores the medical image on which processing is performed by using the processing unit.

According to the seventh aspect, the selected image storage unit can store the medical image processed by the processing unit.

The selected image storage unit may store the processed image on which the processing result is superimposed as the medical image using the processing unit, or may store the processing result as a file separate from the medical image.

According to an eighth aspect, in the medical image processing device according to any one of the first to seventh aspects, the medical image processing device may be configured to comprise an image quality evaluation unit that evaluates an image quality of the medical image acquired by using the image acquisition unit, in which the selection unit selects a medical image according to an image quality evaluation result of the medical image using the image quality evaluation unit.

According to the eighth aspect, the selection unit can select the medical image according to the image quality of the medical image.

According to a ninth aspect, in the medical image processing device according to the eighth aspect, the image quality evaluation unit may be configured to evaluate at least one of blurriness, shake, brightness, presence or absence of noise, or sharpness of a medical image to be evaluated.

According to the ninth aspect, the selection unit can select a medical image whose image quality is evaluated by applying at least one of the viewpoints of blurriness, shake, brightness, presence or absence of noise, or sharpness.

According to a tenth aspect, in the medical image processing device according to any one of the first to ninth aspects, the selection unit may be configured to select a medical image on the basis of a period between an acquisition timing of the user input signal and a timing at which the medical image is acquired by using the image acquisition unit.

According to the tenth aspect, the selection unit can select a medical image acquired in the shortest period from the acquisition timing of the user input signal.

According to an eleventh aspect, in the medical image processing device according to any one of the first to tenth aspects, the recognition processing unit may be configured to detect a region of interest in a medical image to be processed, and the selection unit may be configured to select a medical image in which the region of interest is detected.

According to the eleventh aspect, the recognition unit can apply detection processing of a region of interest as the recognition processing for the medical image.

According to a twelfth aspect, in the medical image processing device according to any one of the first to eleventh aspects, the recognition processing unit may be configured to comprise a classification unit that classifies a medical image to be processed into one or more prescribed classes, and the selection unit may be configured to select a medical image classified into a predetermined class.

According to the twelfth aspect, the classification unit can perform classification processing of the medical image as the recognition processing for the medical image.

The classification result can be expressed by applying the correct answer probability.

According to a thirteenth aspect, in the medical image processing device according to any one of the first to twelfth aspects, the recognition processing unit may be configured to comprise a measurement unit that measures a medical image to be processed, and the selection unit may be configured to select a medical image in which a value measured by using the measurement unit is equal to or more than a predetermined threshold value.

According to the thirteenth aspect, the measurement unit can measure the medical image as the recognition processing for the medical image.

According to a fourteenth aspect, in the medical image processing device according to any one of the first to thirteenth aspects, the acquired image storage unit may be configured to store a plurality of medical images acquired by using the image acquisition unit in a prescribed period.

According to the fourteenth aspect, the selection unit can select a plurality of medical images stored in the acquired image storage unit as images to be selected.

According to a fifteenth aspect, in the medical image processing device according to any one of the first to thirteenth aspects, the acquired image storage unit may be configured to update a medical image to be stored according to a result of the recognition processing using the recognition processing unit for a plurality of medical images acquired by using the image acquisition unit in a prescribed period.

According to the fifteenth aspect, the selection unit can select the latest medical image stored in the acquired image storage unit as images to be selected.

A processor device according to a sixteenth aspect is a processor device comprising an endoscope control unit that controls an endoscope; an image acquisition unit that acquires a medical image; an acquired image storage unit that stores the medical image acquired by using the image acquisition unit; a recognition processing unit that performs recognition processing on the medical image acquired by using the image acquisition unit; a user input signal acquisition unit that acquires a user input signal transmitted according to an operation of a user; and a selection unit that selects a medical image from medical images for which a result of the recognition processing related to a region of interest is obtained in the recognition processing performed by using the recognition processing unit in a case where the user input signal is acquired.

According to the sixteenth aspect, the same effect as in the first aspect can be obtained.

In the sixteenth aspect, the same matters as the matters specified in the second to fifteenth aspects can be appropriately combined. In this case, a component responsible for processing or a function specified in the medical image processing device can be grasped as a component of a processor device responsible for the corresponding processing or function.

An endoscope system according to a seventeenth aspect is an endoscope system comprising an endoscope; a processor device that controls the endoscope; and a medical image processing device that performs processing on an endoscopic image acquired by using the endoscope, in which the medical image processing device includes an endoscope control unit that controls the endoscope; an image acquisition unit that acquires a medical image; an acquired image storage unit that stores the medical image acquired by using the image acquisition unit; a recognition processing unit that performs recognition processing on the medical image acquired by using the image acquisition unit; a user input signal acquisition unit that acquires a user input signal transmitted according to an operation of a user; and a selection unit that selects a medical image from medical images for which a result of the recognition processing related to a region of interest is obtained in the recognition processing performed by using the recognition processing unit in a case where the user input signal is acquired.

According to the seventeenth aspect, the same effect as in the first aspect can be obtained.

In the seventeenth aspect, the same matters as the matters specified in the second to fifteenth aspects can be appropriately combined. In this case, a component responsible for processing or a function specified in the image processing device can be grasped as a component of an endoscope system responsible for the corresponding processing or function.

A medical image processing method according to an eighteenth aspect is a medical image processing method including: an image acquisition step of acquiring a medical image; an acquired image storage step of storing the medical image acquired in the image acquisition step; a recognition processing step of performing recognition processing on the medical image acquired in the image acquisition step; a user input signal acquisition step of acquiring a user input signal transmitted according to an operation of a user; and a selection step of selecting a medical image from medical images for which a result of the recognition processing related to a region of interest is obtained in the recognition processing performed in the recognition processing step in a case where the user input signal is acquired.

According to the eighteenth aspect, the same effect as in the first aspect can be obtained.

In the eighteenth aspect, the same matters as the matters specified in the second to fifteenth aspects can be appropriately combined. In this case, the component responsible for the processing or the function specified in the medical image processing device can be grasped as a component of a medical image processing method responsible for the corresponding processing or function.

A program according to a nineteenth aspect is a program for causing a computer to implement: an image acquisition function of acquiring a medical image; an acquired image storage function of storing the medical image acquired by using the image acquisition function; a recognition processing function of performing recognition processing on a region of interest of the medical image acquired by using the image acquisition function; a user input signal acquisition function of acquiring a user input signal transmitted according to an operation of a user; and a selection function that selects a medical image from medical images for which a result of the recognition processing related to a region of interest is obtained in the recognition processing performed by using the recognition processing function, in a case where the user input signal is acquired.

According to the nineteenth aspect, the same effect as in the first aspect can be obtained.

In the nineteenth aspect, the same matters as the matters specified in the second to fifteenth aspects can be appropriately combined. In this case, the component responsible for the processing or the function specified in the medical image processing device can be grasped as a component of a program responsible for the corresponding processing or function.

According to the present invention, a medical image is selected from the medical images for which the result of the recognition processing related to the region of interest is obtained. As a result, the selection unit can obtain the recognition result and can select a medical image in which the recognition result matches an intention of an operator.

DESCRIPTION OF THE PREFERRED EMBODIMENTS

Hereinafter, preferred embodiments of the present invention will be described in detail with reference to the accompanying drawings. In this specification, the same components are denoted by the same reference numbers, and an overlapping description will be omitted as appropriate.

Overall Configuration of Endoscope System

Figure 1:
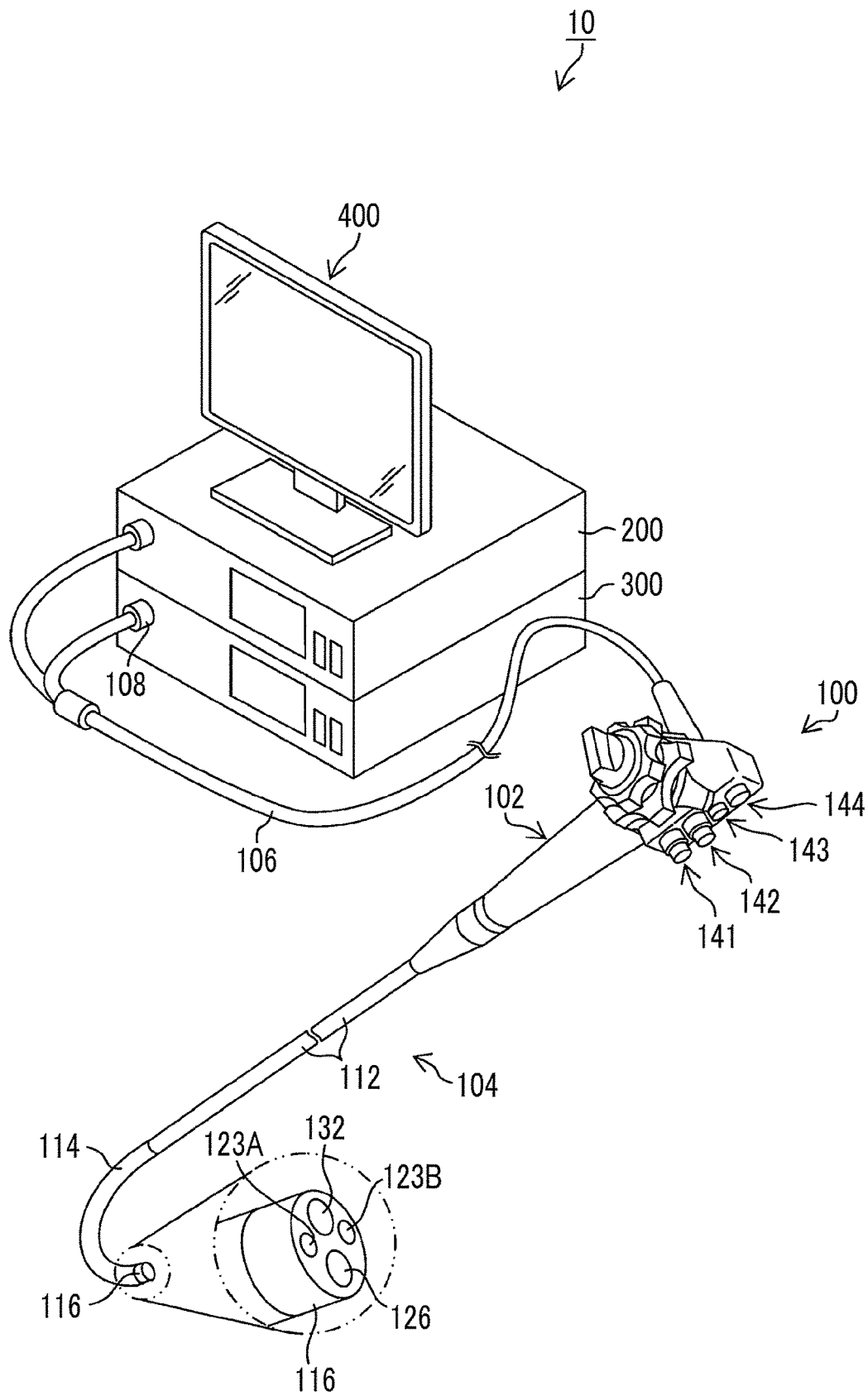
FIG. 1 is an overall configuration diagram of an endoscope system including a medical image processing device according to an embodiment.

FIG. 1 is an overall configuration diagram of an endoscope system including a medical image processing device according to an embodiment. An endoscope system 10 comprises an endoscope main body 100, a processor device 200, a light source device 300, and a monitor 400. A portion of a distal end rigid portion 116 included in the endoscope main body 100 is enlarged and shown in the same figure.

Configuration Example of Endoscope Main Body

The endoscope main body 100 comprises a hand operation portion 102 and an insertion portion 104. A user grasps and operates the hand operation portion 102, inserts the insertion portion 104 into a body of a subject, and observes the body of the subject. The user is synonymous with a doctor, a practitioner, and the like. In addition, the subject here is synonymous with a patient and an examinee.

The hand operation portion 102 comprises an air supply and water supply button 141, a suction button 142, a function button 143, and an imaging button 144. The air supply and water supply button 141 receives operations of an air supply command and a water supply command.

The suction button 142 receives a suction command. Various functions are assigned to the function button 143. The function button 143 receives commands of various functions. The imaging button 144 receives an imaging command operation. The imaging includes moving image capturing and still image capturing.

The insertion portion 104 comprises a flexible portion 112, a bendable portion 114, and the distal end rigid portion 116. The flexible portion 112, the bendable portion 114, and the distal end rigid portion 116 are disposed in this order of the flexible portion 112, the bendable portion 114, and the distal end rigid portion 116 from the hand operation portion 102 side. That is, the bendable portion 114 is connected to a proximal end side of the distal end rigid portion 116, the flexible portion 112 is connected to a proximal end side of the bendable portion 114, and the hand operation portion 102 is connected to a proximal end side of the insertion portion 104.

The user can change a direction of the distal end rigid portion 116 vertically and horizontally by operating the hand operation portion 102 to bend the bendable portion 114. The distal end rigid portion 116 comprises an imaging portion, an illumination portion, and a forceps port 126.

FIG. 1 shows an imaging lens 132 constituting the imaging portion. In addition, FIG. 1 shows an illuminating lens 123A and an illuminating lens 123B constituting the illumination portion. The imaging portion is denoted by reference number 130 and shown in FIG. 2. In addition, the illumination portion is denoted by reference number 123 and shown in FIG. 2.

Figure 2:
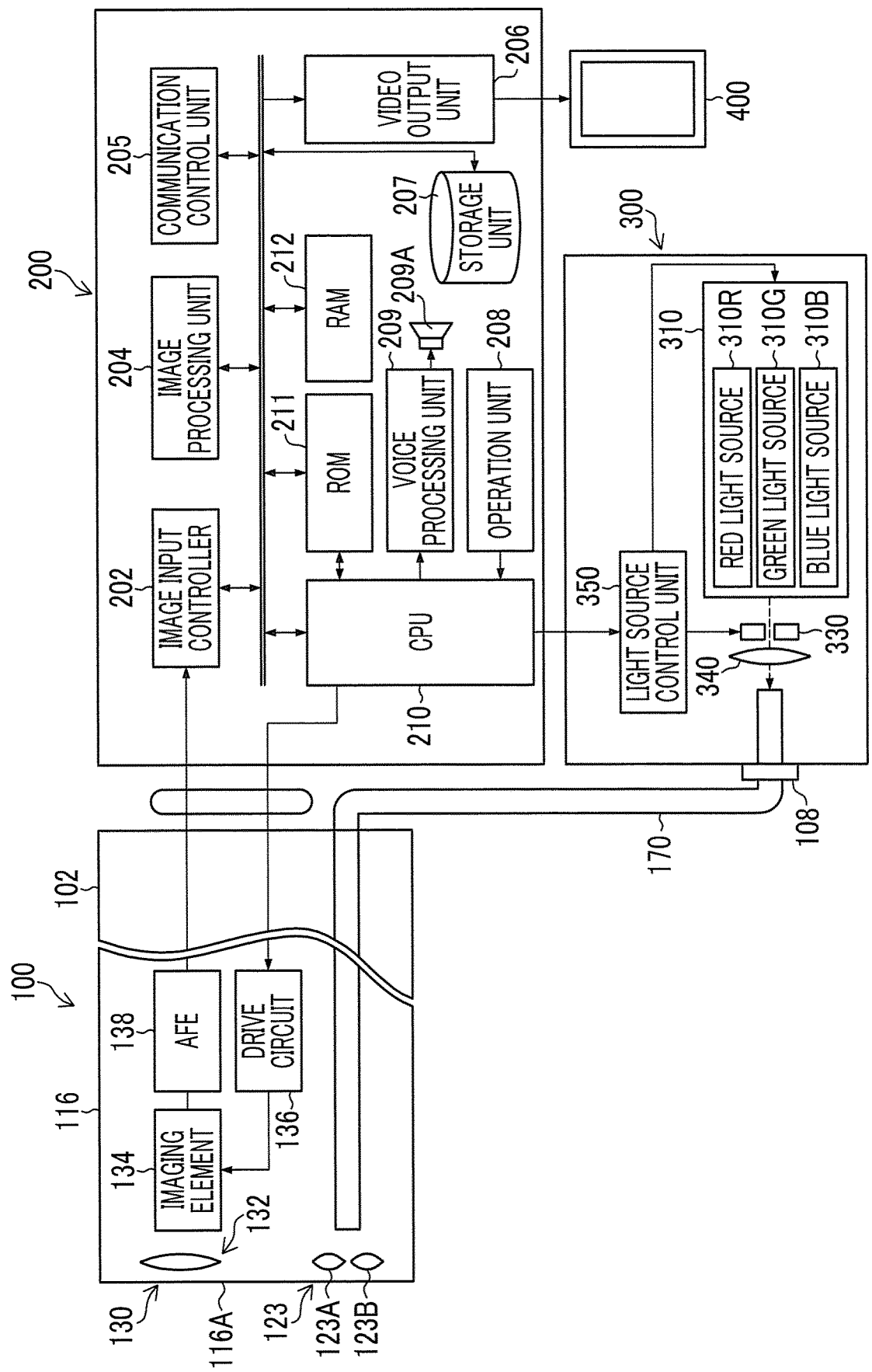
FIG. 2 is a functional block diagram of the endoscope system.

At the time of observation and treatment, at least one of white light or narrow-band light is output via the illuminating lens 123A and the illuminating lens 123B according to an operation of an operation unit 208 shown in FIG. 2.

In a case where the air supply and water supply button 141 is operated, a cleaning water is discharged from a water supply nozzle or a gas is discharged from an air supply nozzle. The cleaning water and the gas are used for cleaning the illuminating lens 123A and the like. The water supply nozzle and the air supply nozzle are not shown. The water supply nozzle and the air supply nozzle may be shared.

The forceps port 126 communicates with a pipe line. A treatment tool is inserted into the pipe line. The treatment tool is supported so that it can be moved back and forth as appropriate. In a case of removing a tumor or the like, the treatment tool is applied to perform necessary treatment.

FIG. 2 is a functional block diagram of the endoscope system. The endoscope main body 100 comprises an imaging portion 130. The imaging portion 130 is disposed inside the distal end rigid portion 116. The imaging portion 130 comprises the imaging lens 132, an imaging element 134, a drive circuit 136, and an analog front end 138. AFE shown in FIG. 2 is an abbreviation for analog front end.

The imaging lens 132 is disposed on a distal-side end surface 116A of the distal end rigid portion 116. An imaging element 134 is disposed at a position opposite to the distal-side end surface 116A of the imaging lens 132. A CMOS type image sensor is applied to the imaging element 134. The CCD type image sensor may be applied to the imaging element 134. CMOS is an abbreviation for complementary metal-oxide semiconductor. CCD is an abbreviation for charge coupled device.

A color imaging element is applied to the imaging element 134. An example of the color imaging element includes an imaging element comprising a color filter corresponding to RGB. The RGB is an acronym for red, green, and blue.

The imaging element 134 may be applied to a monochrome imaging element. In the case where the monochrome imaging element is applied to the imaging element 134, the imaging portion 130 can perform frame-sequential or color-sequential imaging by switching a wavelength range of incidence ray of the imaging element 134.

The drive circuit 136 supplies various timing signals necessary for operation of the imaging element 134 to the imaging element 134 on the basis of a control signal transmitted from the processor device 200.

The analog front end 138 comprises an amplifier, a filter, and an AD converter. AD is an acronym for analog and digital. The analog front end 138 subjects an output signal of the imaging element 134 to processing such as amplification, noise removal, and analog-digital conversion. The output signal of the analog front end 138 is transmitted to the processor device 200.

An optical image to be observed is formed on a light receiving surface of the imaging element 134 via the imaging lens 132. The imaging element 134 converts the optical image to be observed into an electric signal. The electric signal output from the imaging element 134 is transmitted to the processor device 200 via a signal line.

An illumination portion 123 is disposed on the distal end rigid portion 116. The illumination portion 123 comprises the illuminating lens 123A and the illuminating lens 123B. The illuminating lens 123A and the illuminating lens 123B are disposed at positions adjacent to the imaging lens 132 on the distal-side end surface 116A.

The illumination portion 123 comprises a light guide 170. An emission end of the light guide 170 is disposed at a position opposite to the distal-side end surface 116A of the illuminating lens 123A and the illuminating lens 123B.

The light guide 170 is inserted into the insertion portion 104, the hand operation portion 102, and a universal cable 106 shown in FIG. 1. An incident end of the light guide 170 is disposed inside a light guide connector 108.

Configuration Example of Processor Device

The processor device 200 comprises an image input controller 202, an image processing unit 204, and a video output unit 206. The image input controller 202 acquires an electric signal corresponding to the optical image to be observed, which is transmitted from the endoscope main body 100.

The image processing unit 204 generates an endoscopic image to be observed on the basis of an imaging signal which is the electric signal corresponding to the optical image to be observed. The term image in this specification may include the meaning of an image itself and image data representing the image. The images may include moving images and still images. The endoscopic image is denoted by reference number 38 and shown in FIG. 3.

The image processing unit 204 can perform image quality correction by applying digital signal processing such as white balance processing and shading correction processing to the imaging signal. The image processing unit 204 may add accessory information prescribed by DICOM standard to the endoscopic image. The DICOM is an abbreviation for digital imaging and communications in medicine.

The video output unit 206 transmits a display signal representing the image generated by using the image processing unit 204 to the monitor 400. The monitor 400 displays an image to be observed.

In a case where the imaging button 144 shown in FIG. 1 is operated, the processor device 200 operates the image input controller 202, the image processing unit 204, and the like according to an imaging command signal transmitted from the endoscope main body 100.

In a case of acquiring the freeze command signal representing the still image capturing from the endoscope main body 100, the processor device 200 applies the image processing unit 204 to generate a still image based on a frame image at an operation timing of the imaging button 144. The processor device 200 displays the still image using the monitor 400. The frame image is denoted by reference number 38B and shown in FIG. 3. The still image is denoted by reference number 39 and shown in FIG. 3.

The processor device 200 comprises a communication control unit 205. The communication control unit 205 controls communication with a device communicatively connected via a hospital system, a hospital LAN, or the like. The communication control unit 205 can apply a communication protocol based on the DICOM standard. An example of the hospital system includes a hospital information system (HIS). LAN is an abbreviation for local area network.

The processor device 200 comprises a storage unit 207. The storage unit 207 stores the endoscopic image generated using the endoscope main body 100. The storage unit 207 may store various kinds of information incidental to the endoscopic image.

The processor device 200 comprises the operation unit 208. The operation unit 208 outputs a command signal corresponding to a user operation. The operation unit 208 can apply a keyboard, a mouse, a joystick, or the like.

The processor device 200 comprises a voice processing unit 209 and a speaker 209A. The voice processing unit 209 generates a voice signal representing information notified as voice. The speaker 209A converts the voice signal generated by using the voice processing unit 209 into voice. Examples of the voice output from the speaker 209A include a message, a voice guidance, and a warning sound.

The processor device 200 comprises a CPU 210, a ROM 211 and a RAM 212. CPU is an abbreviation for central processing unit. ROM is an abbreviation for read only memory. RAM is an abbreviation for random access memory.

The CPU 210 functions as an overall control unit of the processor device 200. The CPU 210 functions as a memory controller that controls the ROM 211 and the RAM 212. The ROM 211 stores various programs and control parameters applied to the processor device 200.

The RAM 212 is applied to a temporary storage region for data in various kinds of processing and a processing region for calculation processing using the CPU 210. The RAM 212 can be applied to a buffer memory in a case where the endoscopic image is acquired.

The processor device 200 performs various types of processing on the endoscopic image generated by using the endoscope main body 100, and displays the endoscopic image and various kinds of information incidental to the endoscopic image using the monitor 400. The processor device 200 stores the endoscopic image and the various information incidental to the endoscopic image.

That is, in an endoscopy using the endoscope main body 100, the processor device 200 performs the display of an endoscopic image or the like using the monitor 400, the output of voice information using the speaker 209A, and the various types of processing on the endoscopic image.

The processor device 200 can function as a medical image processing device that performs prescribed processing on the medical image by using components such as the image processing unit 204. Examples of the prescribed processing include detection processing of a region of interest, emphasis processing of a region of interest, classification processing of a region of interest, and measurement processing of a region of interest.

Hardware Configuration of Processor Device

The processor device 200 may be applied to a computer. The computer may implement the functions of the processor device 200 by applying the following hardware and executing a prescribed program. The program is synonymous with software.

The processor device 200 can apply various processors as a signal processing unit that performs signal processing. Examples of the processor include a CPU and a graphics processing unit (GPU). The CPU is a general-purpose processor that executes a program and functions as a signal processing unit. GPU is a processor specialized in image processing. As the hardware of the processor, an electric circuit in which electric circuit elements such as semiconductor elements are combined is applied. Each control unit comprises the ROM that stores programs and the like, and the RAM that is a work region for various calculations.

Two or more processors may be applied to one signal processing unit. The two or more processors may be the same type of processor or different types of processors. Further, one processor may be applied to a plurality of signal processing units. The processor device 200 described in the embodiment corresponds to an example of an endoscope control unit.

Configuration Example of Light Source Device

The light source device 300 comprises a light source 310, a stop 330, a condensing lens 340, and a light source control unit 350. The light source device 300 makes observation light incident on the light guide 170. The light source 310 comprises a red light source 310R, a green light source 310G, and a blue light source 310B. The red light source 310R, the green light source 310G, and the blue light source 310B emit red, green, and blue narrow-band lights, respectively.

The light source 310 can generate illumination light in which the red, green, and blue narrow-band lights are randomly combined. For example, the light source 310 can generate white light by combining the red, green, and blue narrow-band lights. In addition, the light source 310 can generate narrow-band light by combining any two colors of red, green, and blue narrow-band lights.

The light source 310 can generate the narrow-band light by using any one color of red, green, and blue narrow-band lights. The light source 310 may selectively switch and emit the white light or the narrow-band light. The narrow-band light is synonymous with special light. The light source 310 can comprise an infrared light source that emits infrared light, an ultraviolet light source that emits ultraviolet light, and the like.

The light source 310 may employ an aspect comprising a white light source that emits the white light, a filter that causes the white light to pass therethrough, and a filter that causes the narrow-band light to pass therethrough. The light source 310 of such an aspect can selectively emit either the white light or the narrow-band light by switching the filter that causes the white light to pass therethrough, and the filter that causes the narrow-band light to pass therethrough.

The filter that causes the narrow-band light to pass therethrough can include a plurality of filters corresponding to different bands. The light source 310 can selectively switch the plurality of filters corresponding to different bands to selectively emit a plurality of narrow-band lights having different bands.

The light source 310 may apply a type, a wavelength range, or the like corresponding to a type of an object to be observed, a purpose of the observation, or the like. Examples of the type of the light source 310 include a laser light source, a xenon light source, an LED light source, and the like. LED is an abbreviation for light-emitting diode.

In a case where the light guide connector 108 is connected to the light source device 300, observation light emitted from the light source 310 reaches the incident end of the light guide 170 via the stop 330 and the condensing lens 340. The observation light is irradiated at the object to be observed via the light guide 170, the illuminating lens 123A, and the like.

The light source control unit 350 transmits a control signal to the light source 310 and the stop 330 on the basis of the command signal transmitted from the processor device 200. The light source control unit 350 controls an illuminance of the observation light emitted from the light source 310, switching of the observation light, on/off of the observation light, and the like.

Configuration Example of Medical Image Processing Device According to First Embodiment Outline A medical image processing device 14 according to the first embodiment performs recognition processing of the medical image in a system for diagnosing a subject in real time such as the endoscope system 10 shown in FIG. 1. Another example of the system for diagnosing the subject in real time includes a CT device, an MRI device, and an ultrasound diagnostic device.

CT is an abbreviation for computed tomography. MRI is an abbreviation for magnetic resonance imaging. The ultrasound diagnostic device can include devices called an ultrasound examination device and an ultrasound device.

Figure 3:
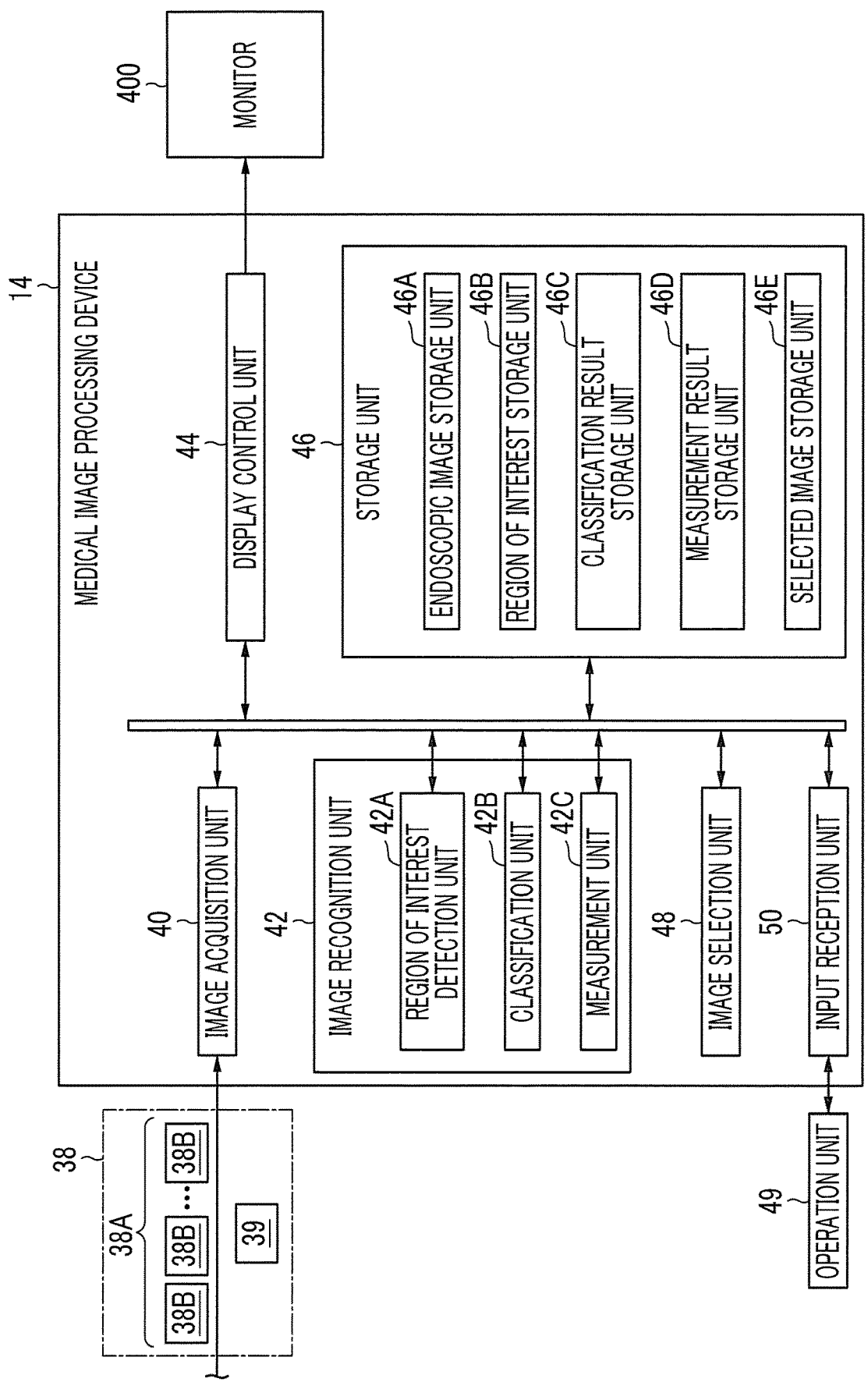
FIG. 3 is a functional block diagram of the medical image processing device.

FIG. 3 is a functional block diagram of a medical image processing device according to the first embodiment. The medical image processing device 14 shown in the figure is implemented by applying the components of the processor device 200 shown in FIG. 2. The medical image processing device 14 comprises an image acquisition unit 40, an image recognition unit 42, a display control unit 44, a storage unit 46, an image selection unit 48, and an input reception unit 50. Hereinafter, each unit will be described.

Image Acquisition Unit

The image acquisition unit 40 acquires the endoscopic image 38 captured by using the endoscope main body 100 shown in FIG. 1. Hereinafter, the acquisition of the endoscopic image 38 can include acquisition of a moving image 38A, acquisition of a frame image 38B, and acquisition of a still image 39.

The image acquisition unit 40 stores the endoscopic image 38 in an endoscopic image storage unit 46A. The image acquisition unit 40 may acquire the endoscopic image 38 from the processor device 200 via a cable that transmits a signal representing the endoscopic image 38.

The image acquisition unit 40 may acquire the endoscopic image 38 from the processor device 200 via an information storage medium such as a memory card. The image acquisition unit 40 may acquire the endoscopic image 38 via a communication network.

The image acquisition unit 40 can acquire the moving image 38A composed of the time-series frame image 38B. The image acquisition unit 40 can acquire the still image 39 in a case where the still image is captured while the moving image 38A is being captured. The image acquisition unit 40 corresponds to the image input controller 202 shown in FIG. 2.

Image Recognition Unit

The image recognition unit 42 comprises a region of interest detection unit 42A, a classification unit 42B, and a measurement unit 42C. The image recognition unit 42 performs recognition processing on the frame image 38B constituting the endoscopic image 38. The image recognition unit 42 stores a recognition result for each frame image 38B. The image recognition unit 42 may store a recognition result representing that the frame image 38B for which the recognition result is not obtained cannot be recognized. The image recognition unit 42 may not store the recognition result for the frame image 38B for which the recognition result is not obtained.

The image recognition unit 42 can perform the recognition processing in real time on the frame image 38B acquired by using the image acquisition unit 40. The image recognition unit 42 may perform the recognition processing on the frame image 38B stored in advance. The image recognition unit 42 corresponds to the image processing unit 204 shown in FIG. 2. The image recognition unit 42 described in the embodiment corresponds to an example of the recognition processing unit. The same applies to an image recognition unit 43 shown in FIG. 12.

The region of interest detection unit 42A applies a learning device such as a convolutional neural network (CNN) to detect a region of interest from the frame image 38B acquired by using the image acquisition unit 40. The region of interest detection unit 42A stores a detection result of the region of interest detected from the frame image 38B in a region of interest storage unit 46B.

As the region of interest detection unit 42A, a learned learning device that has performed learning using a pair of the frame image 38B and position information on the region of interest in the frame image 38B as learning data is applied. Examples of detection of the region of interest include the detection of lesions and detection of specific organs.

The region of interest detection unit 42A may set an emphasis display to emphasize the region of interest. That is, the image recognition unit 42 may include an emphasis processing unit that performs processing to emphasize the region of interest. The emphasis processing unit specifies a position of the region of interest and defines a position of the emphasis display according to the position of the region of interest. The emphasis processing unit specifies a size of the region of interest and defines a size of the emphasis display according to the size of the region of interest. The emphasis processing unit can store emphasis display information including the position of emphasis display and the size of emphasis display in association with the region of interest.

The emphasis processing unit may apply, to the emphasis display, a superimposed display of the closed curve surrounding at least a portion of the region of interest, a superimposed display of the arrow indicating the region of interest, and a superimposed display of the figure at four corners of the region of interest. The emphasis processing unit can apply an emphasis display that adds color, texture, and the like to the region of interest.

The classification unit 42B classifies the region of interest in the frame image 38B. The classification unit 42B stores a classification result for each region of interest in a classification result storage unit 46C in association with the frame image 38B. The classification unit 42B may apply learning devices such as CNN.

The classification unit 42B can apply a learned learning device that has performed learning using the image of the region of interest and the classification result as learning data. Examples of classification of the region of interest include classification of disease types of lesions, classification of organs, classification of regions, and classification of imaging scenes.

The classification unit 42B may specify a disease name of a region of interest that is a lesion. The classification unit 42B can apply standardized classifications such as a union for international cancer control (UICC) and a TNM classification. T in TNM is an acronym for tumor. N in TNM is an acronym for nodes. M in TNM is an acronym for metastasis.

The classification unit 42B described in the embodiment corresponds to an example of a classification unit that classifies the state of the region of interest in the medical image to be processed into one or more prescribed classes.

The measurement unit 42C measures the region of interest in the frame image 38B. The measurement unit 42C stores the measurement result of the region of interest in a measurement result storage unit 46D in association with the frame image 38B. Examples of the measurement of the region of interest include measurement of a size of a lesion, measurement of a size of an organ, and measurement of a distance between the endoscope main body 100 and the region of interest. Examples of the measurement results include measured values. The measurement unit 42C described in the embodiment corresponds to an example of a measurement unit that measures the region of interest in the medical image to be processed.

In the present embodiment, the image recognition unit 42 comprising the region of interest detection unit 42A, the classification unit 42B, and the measurement unit 42C is exemplified, but the image recognition unit 42 can comprise at least one of the region of interest detection unit 42A, the classification unit 42B, or the measurement unit 42C.

Display Control Unit

The display control unit 44 transmits a display signal representing the endoscopic image 38 to be displayed on the monitor 400 to the monitor 400. The display control unit 44 transmits a display signal representing the recognition result of each frame image 38B to the monitor 400. The display control unit 44 transmits a control signal of the monitor 400 to the monitor 400. The display control unit 44 corresponds to the video output unit 206 shown in FIG. 2.

The monitor 400 displays the recognition result of the endoscopic image 38 and each frame image 38B. The recognition result includes at least one of a detection result of the region of interest using the region of interest detection unit 42A, a classification result of the region of interest using the classification unit 42B, or a measurement result of the region of interest using the measurement unit 42C.

The monitor 400 can superimpose and display the recognition result on the endoscopic image 38. The monitor 400 can display a recognition result of the image recognition unit 42 in a region partitioned from a region in which the endoscopic image 38 is displayed. The display control unit 44 updates a display of the endoscopic image 38 and a display of the recognition result of the image recognition unit 42 by applying a prescribed update interval. The details of a display aspect of the endoscopic image 38 will be described later. The display control unit 44 and the monitor 400 described in the embodiment correspond to an example of a display unit.

Storage Unit

The storage unit 46 comprises the endoscopic image storage unit 46A, the region of interest storage unit 46B, the classification result storage unit 46C, the measurement result storage unit 46D, and a selected image storage unit 46E. The endoscopic image storage unit 46A stores the endoscopic image 38 acquired by using the image acquisition unit 40. The storage unit 46 corresponds to the storage unit 207 shown in FIG. 2. The endoscopic image storage unit 46A corresponds to an example of an acquired image storage unit.

The region of interest storage unit 46B stores the detection result of the region of interest detected by using the region of interest detection unit 42A. The region of interest storage unit 46B can store the detection result of the region of interest in association with a frame image 38B in which the region of interest is detected.

As an example of associating the frame image 38B with the detection result of the region of interest, there is an aspect in which an image in which the emphasis display of the region of interest is superimposed on the frame image 38B is stored. As another aspect, there is an aspect in which the detection result of the region of interest is stored in association with the frame image 38B as a file different from the frame image 38B. The same applies to an association between the frame image 38B and information on the classification result and an association between the frame image 38B and the information on the measurement result described below.

The classification result storage unit 46C stores the classification result for each region of interest in association with the frame image 38B. The measurement result storage unit 46D stores the measurement result for each region of interest in association with the frame image 38B.

The selected image storage unit 46E stores the frame image 38B selected by using the image selection unit 48 as the still image 39 in a case where a user command input signal is acquired. Details of the selected image storage unit 46E will be described later.

The storage unit 46 can apply one or more storage elements. That is, the storage unit 46 can comprise four storage elements corresponding to each of the endoscopic image storage unit 46A, the region of interest storage unit 46B, the classification result storage unit 46C, the measurement result storage unit 46D, and a selected image storage unit 46E. In addition, a plurality of storage elements can be applied to each of the endoscopic image storage unit 46A, the region of interest storage unit 46B, the classification result storage unit 46C, the measurement result storage unit 46D, and the selected image storage unit 46E.

Furthermore, any two, three, or four of the endoscopic image storage unit 46A, the region of interest storage unit 46B, the classification result storage unit 46C, the measurement result storage unit 46D, and the selected image storage unit 46E may be configured by using one storage element. All of the endoscopic image storage unit 46A, the region of interest storage unit 46B, the classification result storage unit 46C, the measurement result storage unit 46D, and the selected image storage unit 46E can be configured by using one storage element.

Image Selection Unit

In a case where the user command input signal is acquired during execution of the endoscopy, the image selection unit 48 selects, as the still image 39, a frame image 38B in which an appropriate recognition result related to the region of interest is obtained. The image selection unit 48 corresponds to the image processing unit 204 shown in FIG. 2.

Examples of the frame image 38B in which the appropriate recognition result related to the region of interest is obtained as the still image 39 include the frame image 38B in which the region of interest is detected, a frame image 38B which is classified into a predetermined class, and a frame image 38B in which a value measured by using the measurement unit 42C is equal to or more than a predetermined threshold value.

The medical image processing device 14 stores a plurality of frame images 38B acquired for a certain period during the execution of the endoscopy. The stored plurality of frame images 38B are updated for a certain period.

In the case of acquiring the user command input signal, the medical image processing device 14 selects the frame image 38B in which an appropriate recognition result is obtained from the plurality of stored frame images 38B.

As the appropriate recognition result, in a case where a plurality of recognition result with the correct answer probability is derived, a recognition result having the correct answer probability equal to or more than a predetermined threshold value can be applied. For example, in a case where the maximum value of the correct answer probability is equal to or more than the prescribed threshold value, a recognition result with the maximum value of the correct answer probability can be determined as an appropriate recognition result.

In a case where the user command input signal is a freeze command input signal, the image selection unit 48 selects a frame image 38B in which an appropriate recognition result is obtained from among a plurality of frame images 38B acquired at a timing near an acquisition timing of the freeze command input signal.

The timing near the acquisition timing of the freeze command input signal can include the acquisition timing of the freeze command input signal. The same applies to a timing near an acquisition timing of a still image storage command input signal described below. The nearness here can be applied to a period in which a plurality of frame images in which the same region of interest is the main subject are acquired.

The near timing can be prescribed according to conditions of endoscopy. The conditions of endoscopy can be prescribed on the basis of a frame rate of the endoscopic image 38, a moving speed of the endoscope main body 100, imaging conditions of the object to be observed and the endoscope main body 100, and the like. The moving speed here may be read as a speed that is an absolute value of a moving speed.

In a case where the plurality of frame images 38B correspond to the frame images 38B in which an appropriate recognition result is obtained, the image selection unit 48 can select a frame image 38B in which the correct answer probability is the maximum. In the case where the plurality of frame images 38B correspond to the frame images 38B in which an appropriate recognition result is obtained, the image selection unit 48 can select a frame image 38B at a timing at which the period from the acquisition timing of the user command input signal is the shortest.

The display control unit 44 transmits an image signal representing the frame image 38B selected as the still image 39 by using the image selection unit 48 to the monitor 400. The monitor 400 displays the frame image 38B selected by using the image selection unit 48 as the still image 39 at the acquisition timing of the freeze command input signal for a certain period. A display period setting unit that sets the display period of the still image 39 can be comprised. The display period of the still image 39 can be prescribed according to the acquisition cycle of the medical image, the recognition result of the medical image, and the like.

In a case where the user command input signal is the still image storage command input signal, the image selection unit 48 selects a frame image 38B in which an appropriate recognition result is obtained from among a plurality of frame images 38B at a timing near an acquisition timing of the still image storage command input signal.

The selected image storage unit 46E stores the frame image 38B selected by using the image selection unit 48 as the still image 39 at the acquisition timing of the still image storage command input signal. The selected frame image 38B may be subjected to resolution conversion processing or the like to generate the still image 39 to be selected.

Input Reception Unit

The input reception unit 50 acquires a user command input signal transmitted in a case where a user operates the operation unit 49. The input reception unit 50 transmits the acquired user command input signal to the image selection unit 48.

The operation unit 49 shown in FIG. 3 includes operation buttons and the like that are operated in a case of performing a freeze display and operation buttons and the like that are operated in a case of performing a still image storage. For example, the operation unit 49 shown in FIG. 3 can apply the imaging button 144 shown in FIG. 1. The input reception unit 50 described in the embodiment corresponds to an example of the user input signal acquisition unit.

Procedure of Medical Image Processing Method

Figure 4:
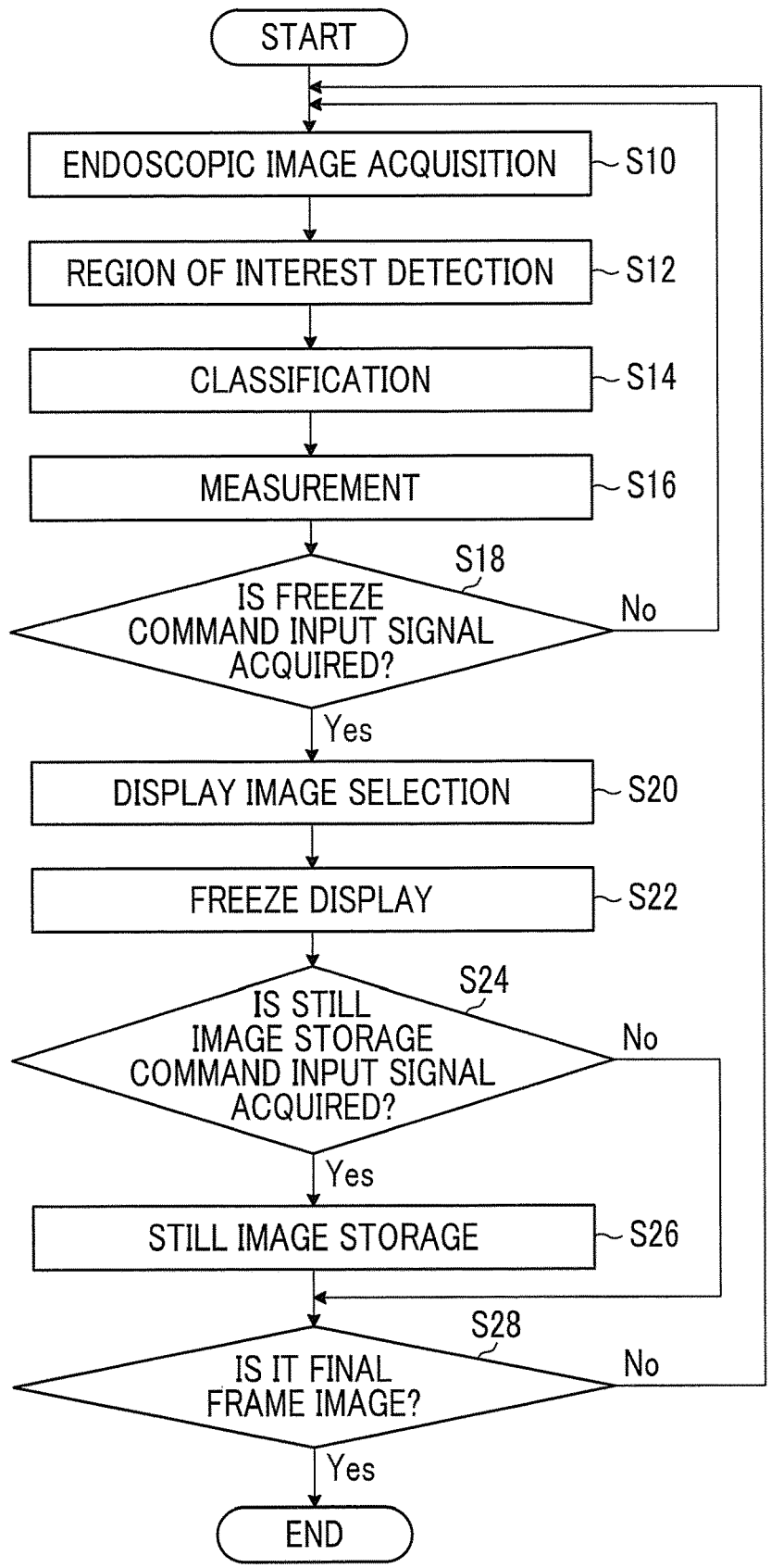
FIG. 4 is a flowchart showing a procedure of a medical image processing method according to a first embodiment.

FIG. 4 is a flowchart showing a procedure of a medical image processing method according to a first embodiment. In an endoscopic image acquisition step S10, the image acquisition unit 40 shown in FIG. 3 acquires the endoscopic image 38. In the endoscopic image acquisition step S10, the image acquisition unit 40 stores the endoscopic image 38 in the endoscopic image storage unit 46A. After the endoscopic image acquisition step S10, the process proceeds to a region of interest detection step S12. The endoscopic image acquisition step S10 described in the embodiment corresponds to an example of the acquired image storage step.

In the region of interest detection step S12, the region of interest detection unit 42A detects a region of interest from each frame image 38B constituting the endoscopic image 38. In the region of interest detection step S12, the region of interest detection unit 42A may detect the region of interest from all the frame images 38B of the moving image 38A, or may detect the region of interest from the frame images 38B in each prescribed period.

In the region of interest detection step S12, the region of interest detection unit 42A stores the detection result of the region of interest in the region of interest storage unit 46B in association with the frame image 38B. After the region of interest detection step S12, the process proceeds to a classification step S14. The region of interest detection step S12 corresponds to an example of a recognition processing step of performing recognition processing on the region of interest.

In the classification step S14, the classification unit 42B classifies the region of interest. In the classification step S14, the classification unit 42B stores a classification result of the region of interest in a classification result storage unit 46C in association with the frame image 38B. After the classification step S14, the process proceeds to a measurement step S16. The classification step S14 corresponds to an example of a recognition processing step of performing recognition processing on the medical image.

In the measurement step S16, the measurement unit 42C measures the region of interest. In the measurement step S16, the measurement unit 42C stores a measurement result of the region of interest in a classification result storage unit 46C in association with the frame image 38B. After the measurement step S16, the process proceeds to a freeze command input signal acquisition determination step S18. At least one of the classification step S14 or the measurement step S16 may be omitted. The measurement step S16 corresponds to an example of a recognition processing step of performing recognition processing on the medical image.

In the freeze command input signal acquisition determination step S18, the input reception unit 50 determines whether or not the freeze command input signal has been acquired. In a case where it is determined in the freeze command input signal acquisition determination step S18 that the input reception unit 50 has not acquired the freeze command input signal, the determination result is No. In the case where the determination result is No, the process returns to the endoscopic image acquisition step S10, and each step from the endoscopic image acquisition step S10 to the freeze command input signal acquisition determination step S18 is repeatedly performed until the determination result is Yes in the freeze command input signal acquisition determination step S18.

on the other hand, in a case where it is determined in the freeze command input signal acquisition determination step S18 that the input reception unit 50 has acquired the freeze command input signal, the determination result is Yes. In the case where the determination result is Yes, the process proceeds to a display image selection step S20. The freeze command input signal acquisition determination step S18 described in the embodiment corresponds to an example of the user input signal acquisition step.

In the display image selection step S20, the image selection unit 48 selects the frame image 38B to be displayed as the still image 39 selected by corresponding to the acquisition of the freeze command input signal. After the display image selection step S20, the process proceeds to a freeze display step S22.

In the freeze display step S22, the display control unit 44 transmits a display signal representing the frame image 38B selected in the display image selection step S20 to the monitor 400. After the freeze display step S22, the process proceeds to a still image storage determination step S24.

In the still image storage determination step S24, the input reception unit 50 determines whether or not a still image storage command input signal has been acquired. In a case where it is determined in the still image storage determination step S24 that the input reception unit 50 has not acquired the still image storage command input signal, the determination result is No. In the case where the determination result is No, the process proceeds to a final frame image determination step S28.

On the other hand, in a case where it is determined in the still image storage determination step S24 that the input reception unit 50 has acquired the still image storage command input signal, the determination result is Yes. In the case where the determination result is Yes, the process proceeds to a still image storage step S26. The still image storage determination step S24 described in the embodiment corresponds to an example of the user input signal acquisition step.

In the still image storage step S26, the image selection unit 48 stores the frame image 38B selected by corresponding to the acquisition of the still image storage command input signal as the still image 39 in the selected image storage unit 46E. After the still image storage step S26, the process proceeds to the final frame image determination step S28.

In the final frame image determination step S28, the image recognition unit 42 determines whether or not recognition processing has been performed on a final frame image 38B in the endoscopic image 38 acquired by using the image acquisition unit 40.

In a case where it is determined in the final frame image determination step S28 that the image recognition unit 42 has not performed the recognition processing on the final frame image 38B, the determination result is No. In the case where the determination result is No, the process proceeds to the endoscopic image acquisition step S10, and each step from the endoscopic image acquisition step S10 to the final frame image determination step S28 is repeatedly performed until the determination result is Yes in the final frame image determination step S28.

On the other hand, in a case where it is determined in the final frame image determination step S28 that the image recognition unit 42 has performed the recognition processing on the final frame image 38B, the determination result is Yes. In the case where the determination result is Yes, the image recognition unit 42 ends the medical image processing method.

The still image 39 to be stored in the still image storage step S26 may be selected separately from the frame image 38B selected according to the freeze command input signal. For example, the still image storage determination step S24 and the still image storage step S26 may be performed after the measurement step S16.

Display Example of Endoscopic Image

Figure 5:
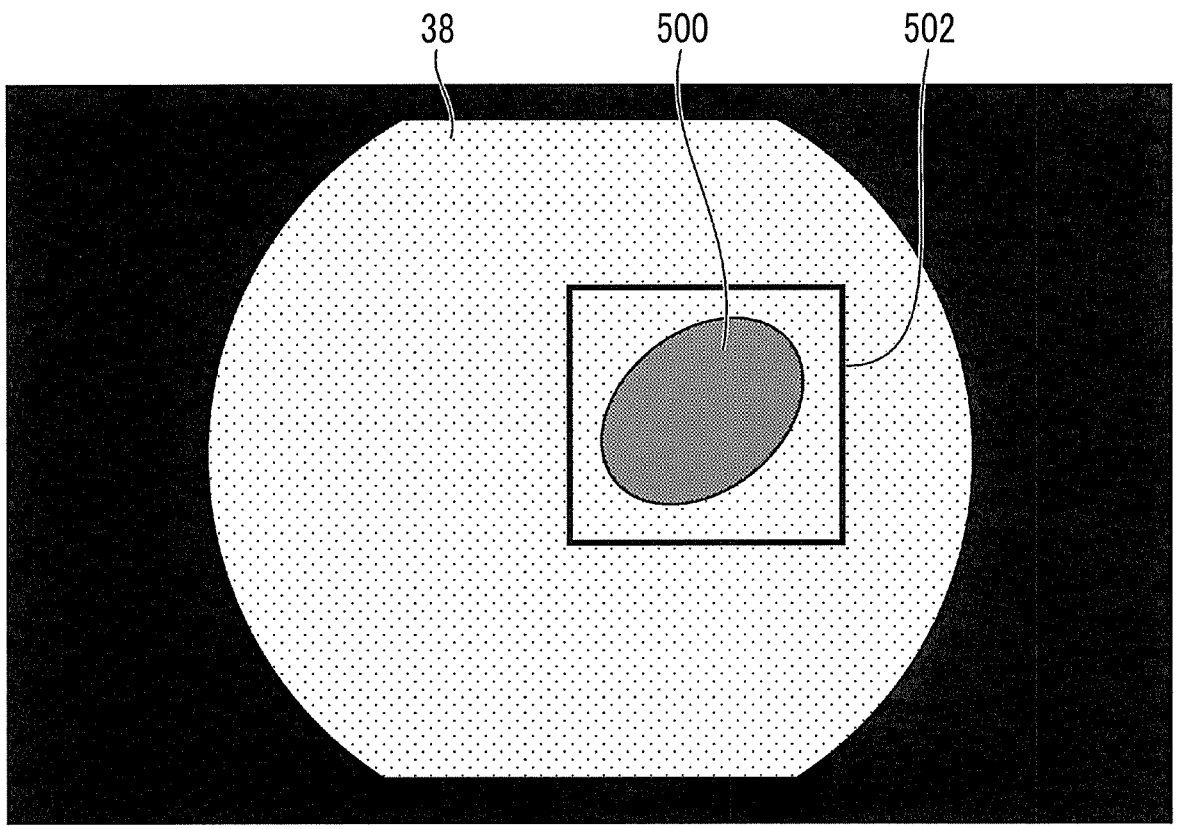
FIG. 5 is a schematic diagram of an endoscopic image showing a display example of a detection result of a region of interest.

FIG. 5 is a schematic diagram of an endoscopic image showing a display example of a detection result of a region of interest. FIG. 5 shows a schematic diagram of an observation image of large intestine as an endoscopic image 38. The same applies to FIGS. 6 and 7. The endoscopic image 38 shown in the figure is displayed on the monitor 400 in a case where the region of interest detection step S12 shown in FIG. 4 is performed.

In the endoscopic image 38 shown in FIG. 5, a lesion is detected as a region of interest 500. In addition, in the endoscopic image 38, a bounding box 502 is superimposed and displayed on the region of interest 500 as an emphasis display for emphasizing the region of interest 500.

Figure 6:
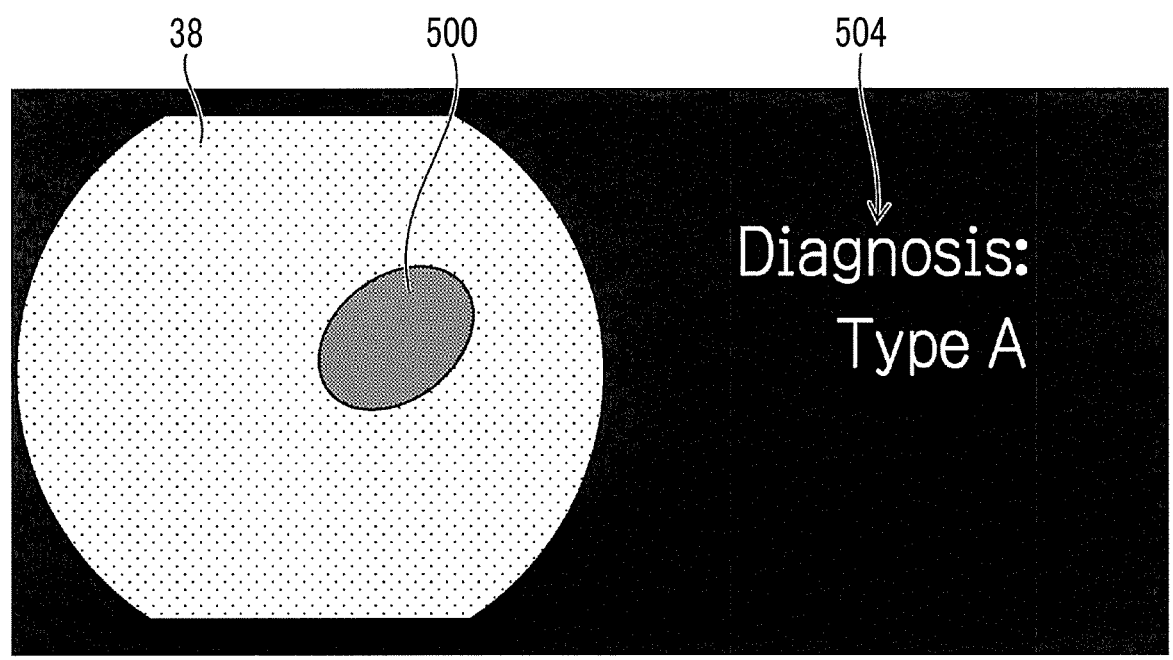
FIG. 6 is a schematic diagram of an endoscopic image showing a display example of a classification result of the region of interest.

FIG. 6 is a schematic diagram of an endoscopic image showing a display example of a classification result of the region of interest. FIG. 6 shows an aspect in which the classification result 504 of the region of interest 500 is displayed in a region different from a display region of the endoscopic image 38.

Character information representing that the diagnosis result of the lesion that is the region of interest 500 is Type A is applied to the classification result 504. The endoscopic image 38 shown in FIG. 6 may display the bounding box 502 shown in FIG. 5. The same applies to the endoscopic image 38 shown in FIG. 7.

Figure 7:
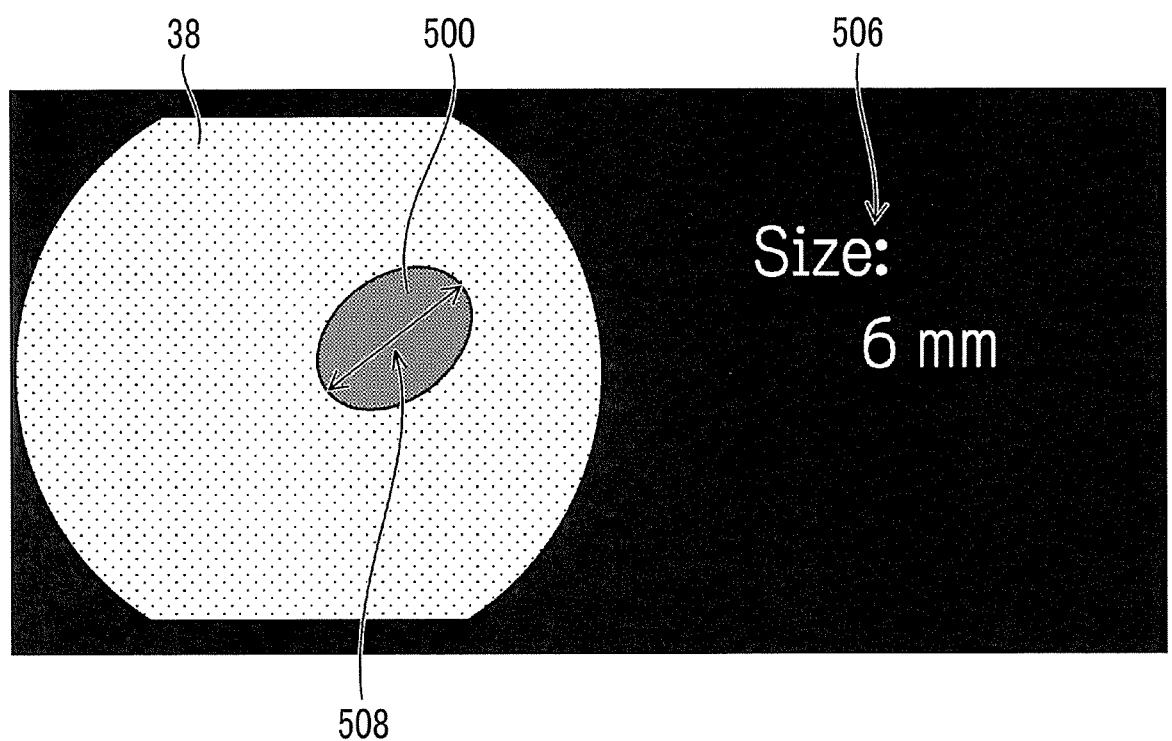
FIG. 7 is a schematic diagram of an endoscopic image showing a display example of a measurement result of the region of interest.

FIG. 7 is a schematic diagram of an endoscopic image showing a display example of a measurement result of the region of interest. FIG. 7 shows aspects in which the measurement result 506 of the region of interest 500 is displayed in the region different from the display region of the endoscopic image 38, and an arrow line 508 indicating the measurement position of the region of interest 500 is superimposed and displayed on the region of interest 500. Characteristic information representing that the maximum size of the lesion that is the region of interest 500 is 6 millimeters is applied to the measurement result 506.

In a case where the still image 39 is stored, the recognition result obtained by using the image recognition unit 42 may be stored in association with the still image 39. For example, as the still image 39, an image in which the emphasis display of the region of interest 500 is superimposed on the frame image 38B corresponding to the endoscopic image 38 shown in FIG. 5 may be generated and stored.

Alternatively, a file representing a recognition result of the region of interest 500 may be created separately from the still image 39, and the still image 39 may be associated with data representing the recognition result. For example, the data representing the recognition result may be stored as a header of the still image 39. The same applies to the classification result 504 shown in FIG. 6 and the measurement result 506 shown in FIG. 7.

Accordingly, the recognition result of the still image 39 can be stored without damaging the still image 39 itself. In addition, the still image 39 using the recognition result of the still image 39 can be arranged. Further, in a case where the still image 39 is displayed again, the recognition result can be displayed.

Also in such an aspect, a display aspect of a recognition result of the frame image 38B to be freeze-displayed and the still image 39 to be stored as a still image may be changed.

In a case where the freeze display of the endoscopic image 38 is performed, the bounding box 502 shown in FIG. 5, the classification result 504 shown in FIG. 6, and the measurement result 506 shown in FIG. 7 are displayed in the frame image 38B to be freeze-displayed. This allows a doctor who is a user to check whether or not a recognition result of the bounding box 502 or the like is appropriate.

The same applies to a case where the still image storage of the endoscopic image 38 is performed. For example, even in a case where the doctor creates a report after storing the still image 39, the doctor can check whether or not the recognition result of the bounding box 502 or the like is appropriate.

The medical image processing device 14 shown in FIG. 3 may change the display aspect of the recognition result from the case of performing the still image storage in the case of performing the freeze display. For example, the bounding box 502 may be displayed in the case where the freeze display is performed, and the classification result 504 may be displayed in the case where the stored still image 39 is displayed.

In a case where displaying the moving image 38A of the endoscopic image 38, the medical image processing device 14 may hide the recognition result. In addition, the moving image 38A of the endoscopic image 38 may change the display aspect of the recognition result from the frame image 38B to be freeze-displayed.

In a case of observing the moving image 38A of the endoscopic image 38 in real time, the doctor wants to observe the lesion in detail, so that the display of the recognition result of the bounding box 502 or the like can hinder the observation of the doctor. Therefore, the recognition result is hidden in the case where the moving image 38A of the endoscopic image 38 is observed in real time, and the recognition result is displayed in the case where the freeze display is performed. Thereby, a more suitable display aspect for the doctor can be implemented.

The medical image processing device 14 can change the display aspect of the recognition result of the frame image 38B to be freeze-displayed and the still image 39 to be stored. In the case where the freeze display is performed, fine structures of the lesion are observed.

On the other hand, the stored still image 39 is applied to creating a report or the like. In the case where the report is created, the still image 39 is displayed list of pictures, and the still image 39 is associated with the classification result, the doctor's findings, and the like.

For example, in a case where lesion detection is performed, the freeze display surrounds the periphery of the lesion using a figure such as the bounding box 502 shown in FIG. 5. As a result, the display of the recognition result does not hinder the observation. On the other hand, in a case of storing the still image 39, a specific color is superimposed and displayed on the entire lesion. This makes it possible to make the lesion stand out even in the case where the still image 39 is displayed list of pictures. In this way, a still image 39 suitable for the doctor's work may be provided.

Figure 8:
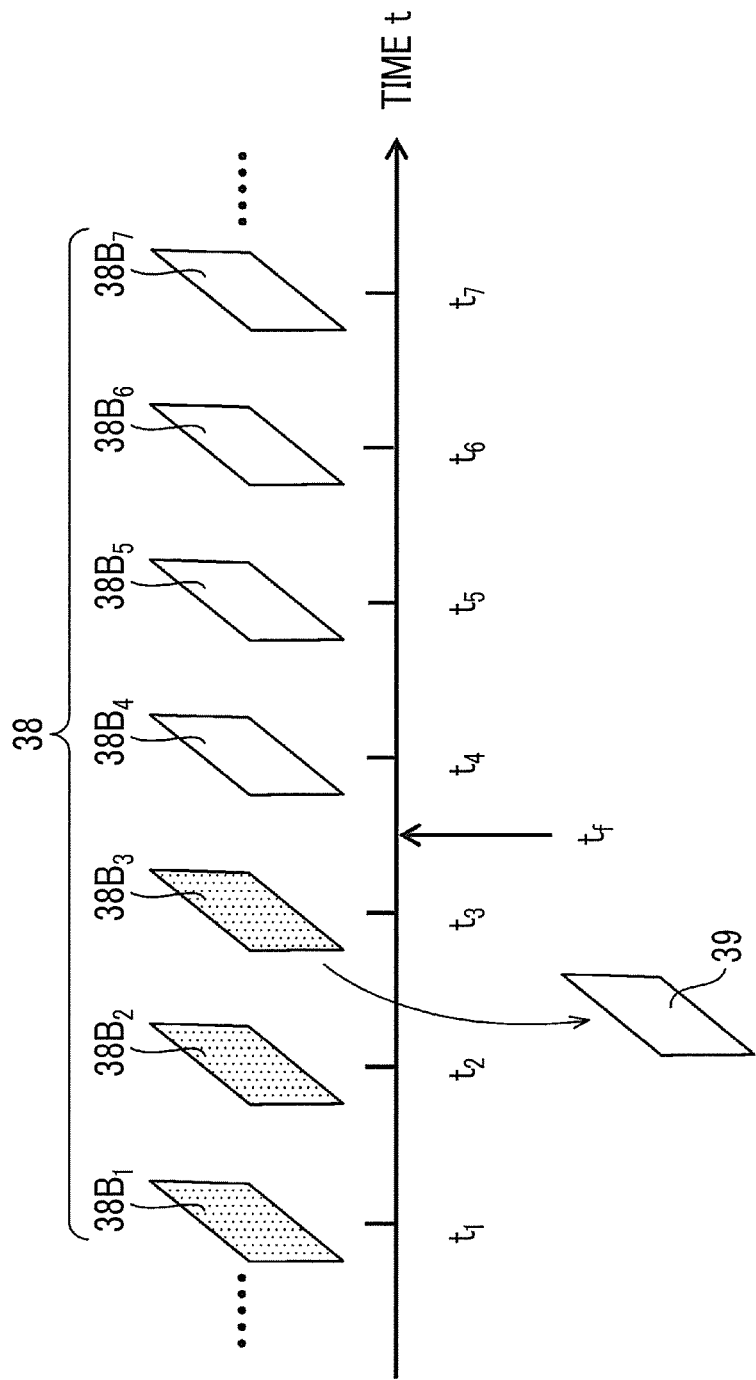
FIG. 8 is a schematic diagram in a case where a frame image before a user command input signal acquisition timing is an image to be selected.
Figure 9:
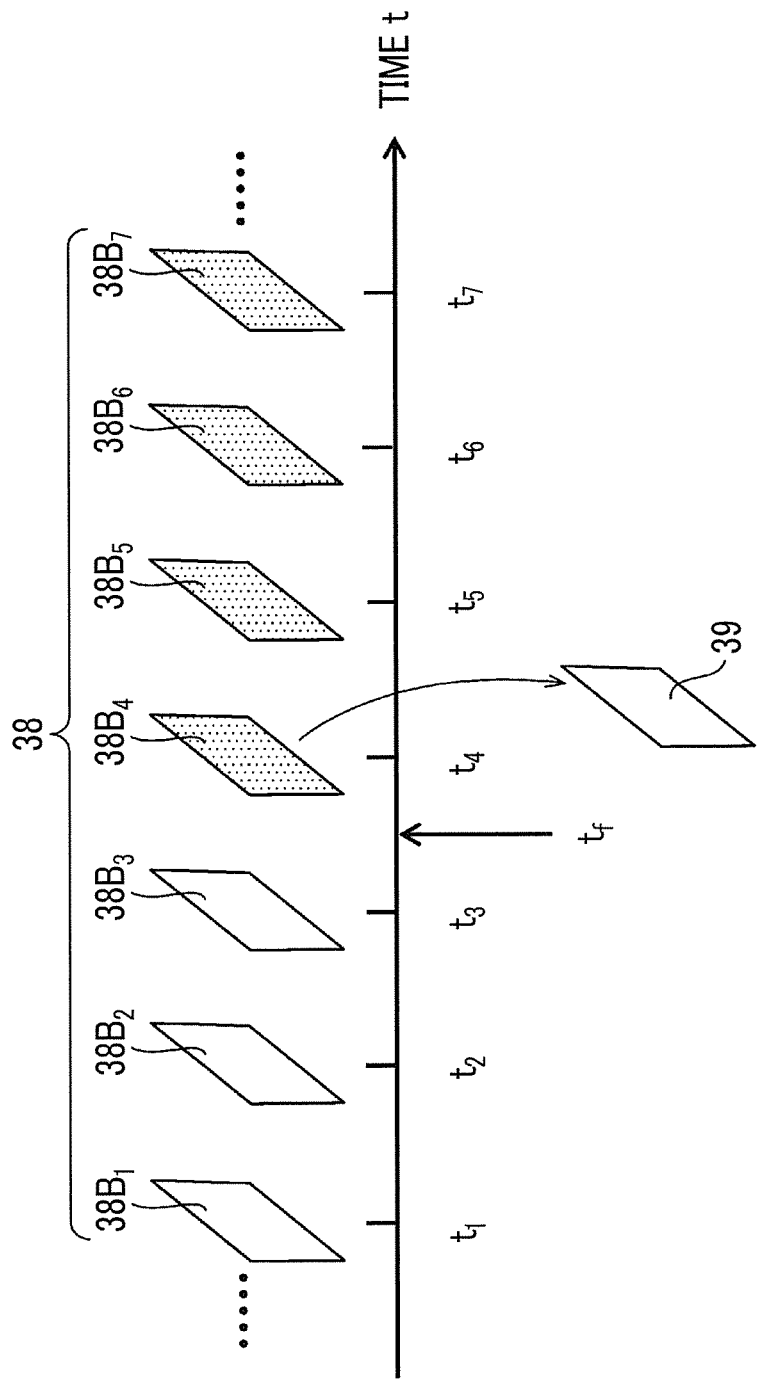
FIG. 9 is a schematic diagram in a case where a frame image after the user command input signal acquisition timing is an image to be selected.
Figure 10:
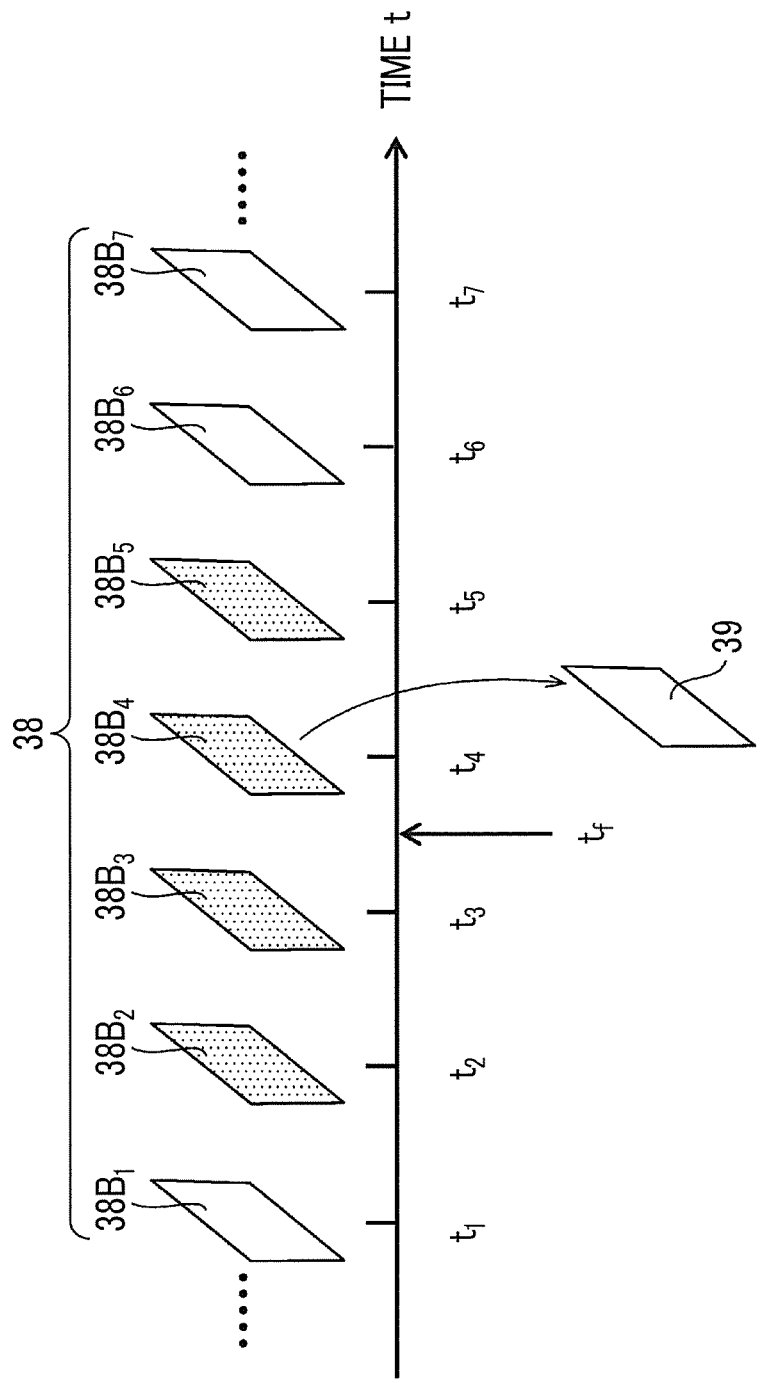
FIG. 10 is a schematic diagram in a case where a frame image before and after the user command input signal acquisition timing is an image to be selected.

Explanation of Frame Image to be Selected FIGS. 8 to 10 are explanatory diagrams of frame images to be selected. FIG. 8 is a schematic diagram in a case where a frame image before a user command input signal acquisition timing is an image to be selected. Each of frame images $38B_1$ to $38B_7$ is stored from timing $t_1$ to timing $t_7$.

In a case where the user command input signal is acquired at a timing $t_f$, the image selection unit 48 shown in FIG. 3 sets the frame image $38B_1$, the frame image $38B_2$, and the frame image $38B_3$ as the frame image 38B to be selected. In the example shown in FIG. 8, the image selection unit 48 selects the frame image $38B_3$ as the still image 39 to be processed according to the user command.

In a case where a plurality of frames constituting the endoscopic image 38 are collectively acquired, the storage timing of each of the frame images 38B shown in FIG. 8 may be read as the imaging timing of the frame image 38B or the generation timing of the frame image 38B. The same applies to FIGS. 9 and 10.

FIG. 9 is a schematic diagram in a case where a frame image after the user command input signal acquisition timing is selected. In the case where the user command input signal is acquired at the timing $t_f$, the image selection unit 48 sets the frame images $38B_4$ to $38B_7$ as the frame image 38B to be selected. In the example shown in FIG. 9, the image selection unit 48 selects the frame image $38B_4$ as the still image 39 to be processed according to the user command.

FIG. 10 is a schematic diagram in a case where a frame image before and after the user command input signal acquisition timing is selected. In the case where the user command input signal is acquired at the timing $t_f$, the image selection unit 48 sets the frame images $38B_2$ to $38B_5$ as the frame image 38B to be selected. In the example shown in FIG. 10, the image selection unit 48 selects the frame image $38B_4$ as the still image 39 to be processed according to the user command.

In aspects shown in FIGS. 8 to 10, in a case where the degrees of priority of the recognition results in the plurality of frame images 38B are the same, the image selection unit 48 can select a frame image 38B according to the period from the timing $t_f$ at which the user command input signal is acquired. For example, a frame image 38B having the shortest period can be selected.

Figure 11:
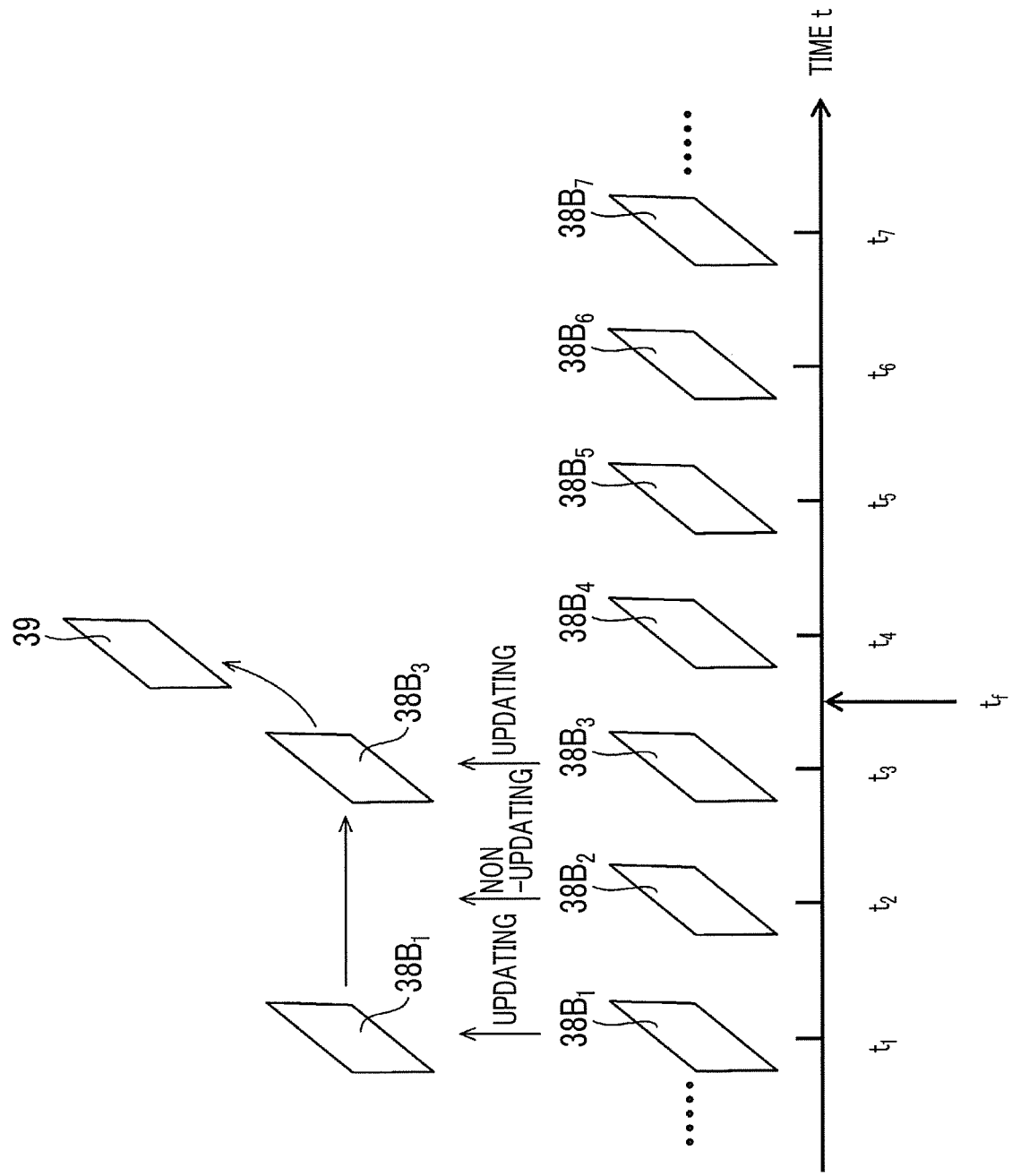
FIG. 11 is a schematic diagram showing another example of a frame image to be selected.

FIG. 11 is a schematic diagram showing another example of a frame image to be selected. In the example shown in FIG. 11, the image selection unit 48 compares the recognition result with the previously stored frame image 38B every time the frame image 38B is acquired, and updates the fame image 38B to be selected on the basis of the comparison result.

The image selection unit 48 selects the frame image 38B stored at the timing $t_f$ at which the user command input signal is acquired, as the still image 39. In the example shown in FIG. 11, the image selection unit 48 updates the frame image 38B to be selected on the basis of the comparison result between the frame image $38B_1$ and the frame image $38B_3$. The image selection unit 48 selects the frame image $38B_3$ stored at the timing $t_f$ at which the user command input signal is acquired, as the still image 39.

In the aspects shown in FIGS. 8 to 11, the certain period in which the plurality of frame images 38B are stored can be prescribed on the basis of the frame rate of the endoscopic image 38, the conditions of endoscopy, a storage capacity of the endoscopic image storage unit 46A, and the like. For example, in a case where the frame rate of the endoscopic image 38 is 60 frames per second, the certain period in which the plurality of frame images 38B are stored can be a random period of 1.0 second or less.

Operation Effect of First Embodiment

The medical image processing device 14 according to the first embodiment can obtain the following operation effect.

[1] In the endoscopy, the recognition processing of the frame image 38B constituting the endoscopic image 38 is performed, the frame image 38B and the recognition result are associated with each other, and the frame image 38B and the recognition result for a certain period are stored. In the case where the user command input signal is acquired, the frame image 38B in which an appropriate recognition result related to the region of interest is obtained is selected as the still image 39 to be processed by the user command. Accordingly, in the case where the user command input signal is acquired, the frame image in which the appropriate recognition result is obtained can be selected as the still image 39 to be processed by the user command.

[2] The user command can apply at least one of the freeze display or the still image storage. As a result, the still image 39 in which the appropriate recognition result is obtained can be displayed and stored.

[3] in the case where the user command is the freeze display, the recognition result is superimposed and displayed on the still image 39. As a result, the doctor can check the recognition result of the still image 39 to be freeze-displayed.

[4] In the case where the user command is the still image storage, the recognition result is stored in association with the still image 39. As a result, the recognition result can be displayed in the case where the stored still image 39 is displayed.

[5] The recognition processing includes at least one of the detection of the region of interest, the classification of the region of interest, or the measurement of the region of interest. As a result, it is possible to select the still image 39 to be processed according to the user command based on at least one of the detection result of the region of interest, the classification result of the region of interest, or the measurement result of the region of interest.

[6] The image selection unit 48 selects the still image 39 to be processed by the user command on the basis of a period between the acquisitions of the user command input signal. As a result, it becomes possible to select the still image 39 to be processed by the user command in consideration of the period between the acquisitions of the user command input signal.

Medical Image Processing Device According to Second Embodiment

Next, a medical image processing device according to the second embodiment will be described. The medical image processing device according to the second embodiment selects the still image 39 to be processed by the user command in consideration of the image quality of the frame image 38B to be selected. Hereinafter, differences between the medical image processing device 14 and the medical image processing method according to the first embodiment will be mainly described.

Figure 12:
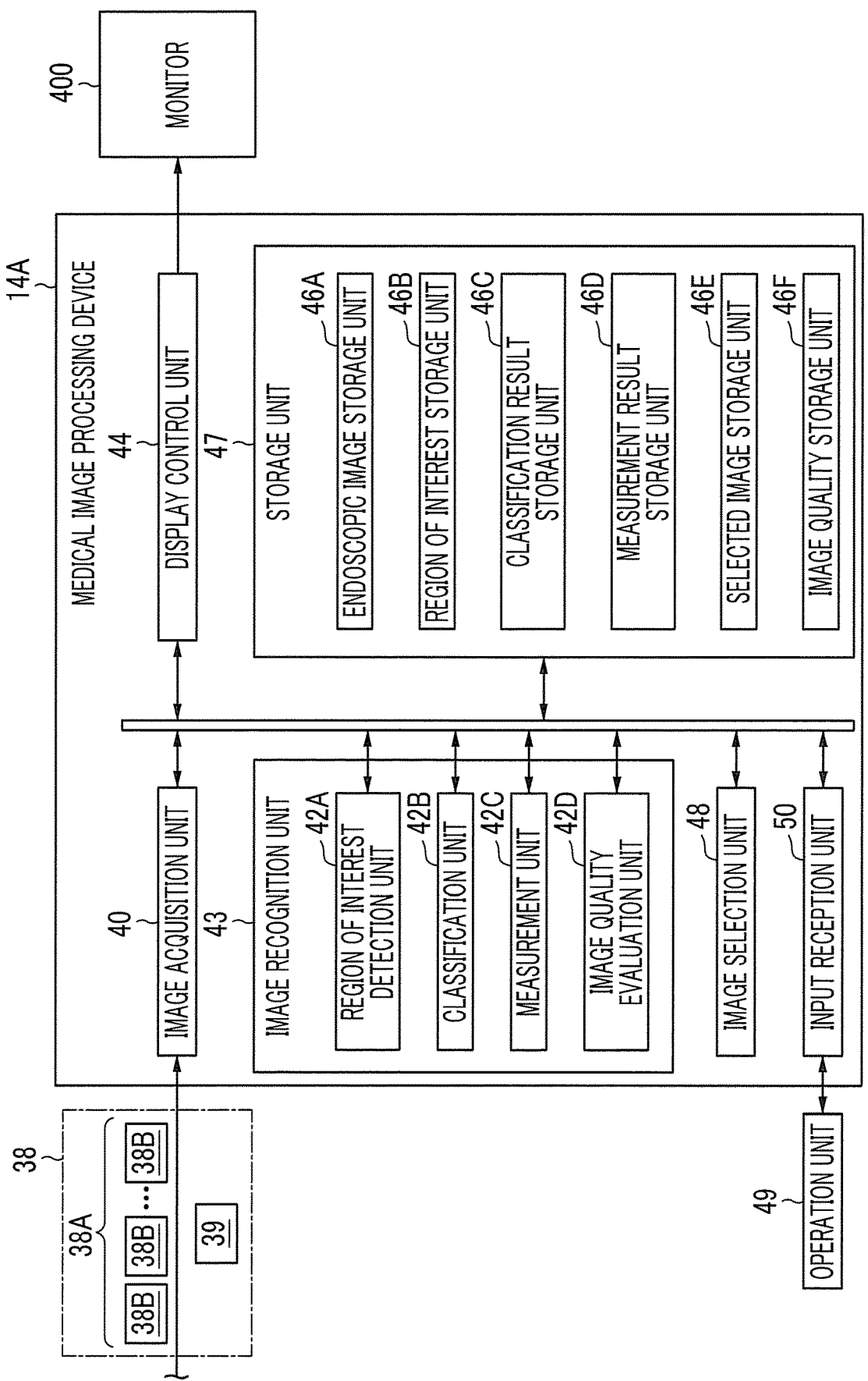
FIG. 12 is a functional block diagram of a medical image processing device according to a second embodiment.

FIG. 12 is a functional block diagram of a medical image processing device according to a second embodiment. A medical image processing device 14A shown in the figure comprises an image recognition unit 43 instead of the image recognition unit 42 shown in FIG. 3.
In addition, the medical image processing device 14A comprises a storage unit 47 instead of the storage unit 46. In the image recognition unit 43, an image quality evaluation unit 42D is added to the image recognition unit 42 shown in FIG. 3. In the storage unit 47, an image quality storage unit 46F is added to the storage unit 46 shown in FIG. 3.

The image quality evaluation unit 42D evaluates the image quality of the frame image 38B in which the recognition result has been obtained. For the image quality evaluation of the frame image 38B, the viewpoint of defocus of the frame image 38B such as presence or absence of defocus and the degree of defocus can be applied.

Other aspects of image quality evaluation include shake, brightness, presence or absence of noise, and sharpness. For shake, the image quality evaluation unit 42D may derive an image quality evaluation value. The image quality evaluation unit 42D may derive an image quality evaluation value for each viewpoint of image quality evaluation. The image quality evaluation unit 42D may derive a comprehensive evaluation value of image quality using a plurality of image quality evaluation values.

The image quality evaluation unit 42D can derive an image quality evaluation value for the frame image 38B to be evaluated. The image quality evaluation unit 42D associates the image quality evaluation with the frame image 38B and stores the image quality evaluation result in the image quality storage unit 46F.

In a case where there are a plurality of frame images 38B for which the recognition result is appropriately determined, the image selection unit 48 can select a frame image 38B having the best image quality from the plurality of frame images 38B. The image quality evaluation value can be applied to weight coefficients in a case of weighting the recognition result.

Figure 13:
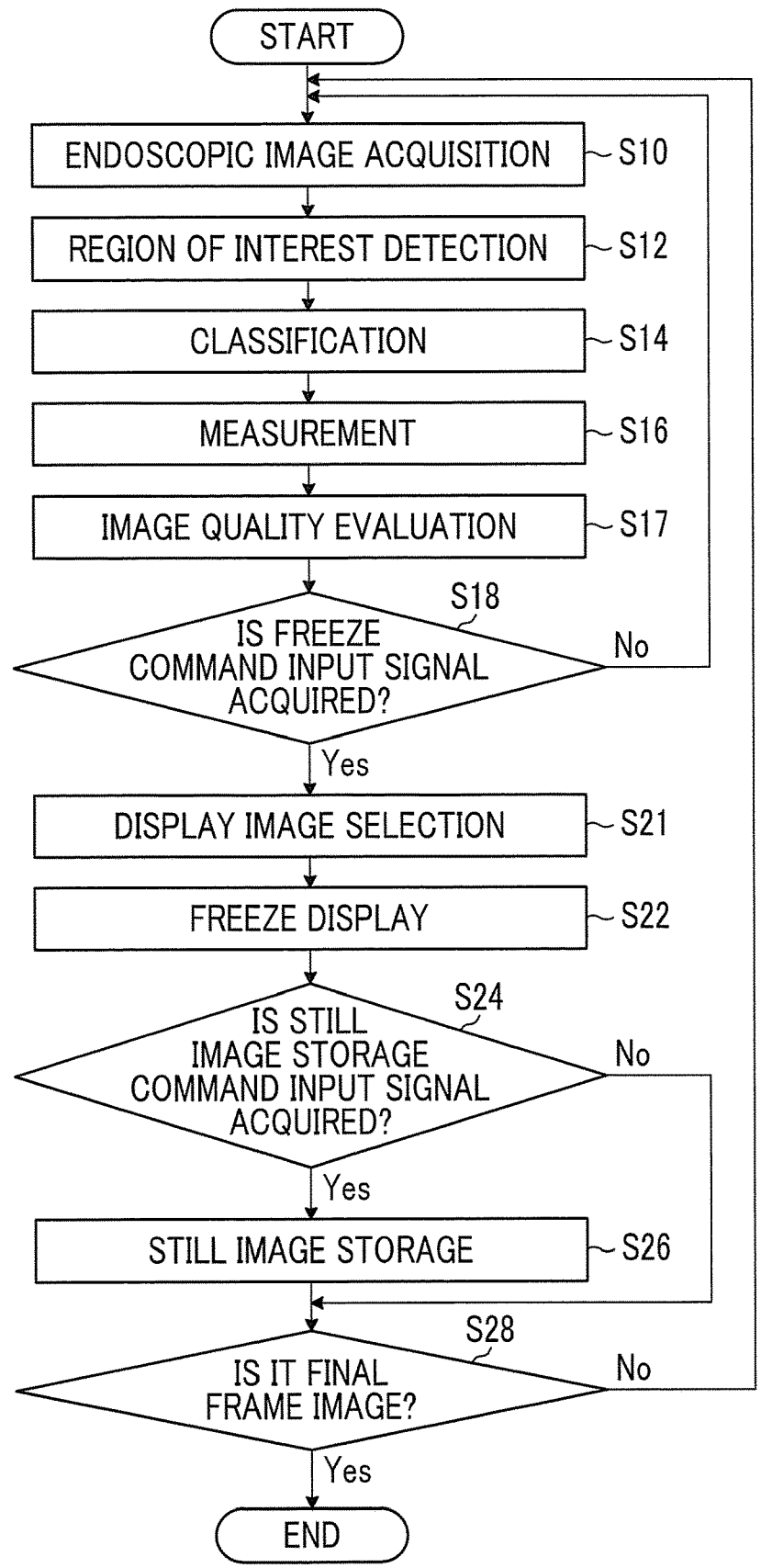
FIG. 13 is a flowchart showing a procedure of a medical image processing method according to the second embodiment.

FIG. 13 is a flowchart showing a procedure of a medical image processing method according to the second embodiment. In the flowchart shown in FIG. 13, an image quality evaluation step S17 is added to the flowchart shown in FIG. 4, and a display image selection step S21 is performed instead of the display image selection step S20.

Each step from the endoscopic image acquisition step S10 to the measurement step S16 in the flowchart shown in FIG. 13 is the same as each step from the endoscopic image acquisition step S10 to the measurement step S16 shown in FIG. 1. Here, these explanations are omitted.

In the flowchart shown in FIG. 13, after the measurement step S16, the process proceeds to the image quality evaluation step S17. In the image quality evaluation step S17, the image quality evaluation unit 42D shown in FIG. 12 evaluates the image quality of the frame image 38B and derives the image quality evaluation value. In the image quality evaluation step S17, the image quality evaluation unit 42D stores the image quality evaluation value in the image quality storage unit 46F. After the image quality evaluation step S17, the process proceeds to the freeze command input signal acquisition determination step S18.

The freeze command input signal acquisition determination step S18 is the same as the flowchart shown in FIG. 4. After the freeze command input signal acquisition determination step S18, the process proceeds to the display image selection step S21. In the display image selection step S21, the image selection unit 48 selects the frame image 38B to be displayed as the still image 39 in consideration of the image quality of the frame image 38B. After the display image selection step S21, the process proceeds to a freeze display step S22.

Each step from the freeze display step S22 to the final frame image determination step S28 is the same as each step from the freeze display step S22 to the final frame image determination step S28 shown in FIG. 4. Here, these explanations are omitted.

Operation Effect of Second Embodiment

The medical image processing device 14A according to the second embodiment can obtain the following operation effect.

[1] The image quality evaluation unit 42D evaluates the image quality of the acquired frame image 38B. In a case where the frame image 38B to be processed corresponding to the user command input signal is selected, the image quality of the frame image 38B is considered. Thereby, an appropriate frame image can be selected as the still image 39 to be processed by the user command.

[2] The image quality evaluation unit 42D derives the image quality evaluation value of the acquired frame image 38B. As a result, a quantitative evaluation result of the frame image 38B can be derived.

Modification Example of Endoscope System

Modification Example of Illumination Light

Examples of medical images that can be acquired by using the endoscope system 10 according to the present embodiment include a normal light image obtained through irradiation of light in a white band or light in a plurality of wavelength ranges as the light in the white band.

Another example of the medical image that can be acquired by using the endoscope system 10 according to the present embodiment includes an image obtained through irradiation of light in a specific wavelength range. For the specific wavelength range, a band narrower than the white band can be applied. The following modification example can be applied.

First Modification Example

A first example of the specific wavelength range is a visible blue band or green band. The wavelength range of the first example includes a wavelength range from 390 nanometers to 450 nanometers, or from 530 nanometers to 550 nanometers, and the light of the first example has a peak wavelength in the wavelength range from 390 nanometers to 450 nanometers, or from 530 nanometers to 550 nanometers.

Second Modification Example

A second example of the specific wavelength range is a visible red band. The wavelength range of the second example includes a wavelength range from 585 nanometers to 615 nanometers, or from 610 nanometers to 730 nanometers, and the light of the second example has a peak wavelength in the wavelength range from 585 nanometers to 615 nanometers, or from 610 nanometers to 730 nanometers.

Third Modification Example

A third example of the specific wavelength range includes a wavelength range in which oxygenated hemoglobin and reduced hemoglobin have different light absorption coefficients, and light of the third example has a peak wavelength in the wavelength range in which oxygenated hemoglobin and reduced hemoglobin have different light absorption coefficients. The wavelength range of the third example includes a wavelength range of $400\pm10$ nanometers, $440\pm10$ nanometers, $470\pm10$ nanometers, or 600 nanometers to 750 nanometers, and light of the third example has a peak wavelength in the wavelength range of $400\pm10$ nanometers, $440\pm10$ nanometers, $470\pm10$ nanometers, or 600 nanometers to 750 nanometers.

Fourth Modification Example

A fourth example of the specific wavelength range is a wavelength range of excitation light used for observation of fluorescence emitted by a fluorescent substance in a living body and exciting the fluorescent substance. For example, it is a wavelength range of 390 nm to 470 nm. The observation of fluorescence may be referred to as fluorescence observation.

Fifth Modification Example

A fifth example of the specific wavelength range is a wavelength range of infrared light. The wavelength range of the fifth example includes a wavelength range of 790 nanometers to 820 nanometers, or 905 nanometers to 970 nanometers, and the light of the fifth example has a peak wavelength in a wavelength range of 790 nanometers to 820 nanometers, or 905 nanometers to 970 nanometers.

Generation Example of Special Light Image

The processor device 200 may generate a special light image having information on a specific wavelength range on the basis of a normal light image obtained by capturing an image using white light. The generation here includes acquisition. In this case, the processor device 200 functions as a special light image acquisition unit. Then, the processor device 200 obtains a signal in the specific wavelength range by performing a calculation based on the color information on red, green and blue, or cyan, magenta and yellow included in the normal light image.

Cyan, magenta, and yellow may be expressed as CMY using an acronym for cyan, magenta, and yellow, respectively.

Generation Example of Feature Quantity Image

As a medical image, a feature quantity image can be generated by using a calculation based on at least one of a normal image obtained through irradiation of light of a white band or light of a plurality of wavelength ranges as the light of the white band or a special light image obtained through irradiation of light of a specific wavelength range.

In the above-described embodiment and modification example, the endoscopic image is exemplified as an example of the medical image, but a CT image, an MRI image, an ultrasound image, or the like may be applied as the medical image.

Application Example to Program that Cause Computer to Function as Medical Image Processing Device The medical image processing device and the medical image processing method described above can be configured as a program that causes a computer to implement functions corresponding to each unit in the medical image processing device or each step in the medical image processing method.

For example, a program can be configured to cause a computer to implement an image acquisition function, an acquired image storage function, a recognition processing function, a user input signal acquisition function, and a selection function. The image acquisition function corresponds to the image acquisition unit 40 and the endoscopic image acquisition step S10.

The acquired image storage function corresponds to the endoscopic image storage unit 46A and the endoscopic image acquisition step S10. The recognition processing function corresponds to the image recognition unit 42, the region of interest detection step S12, the classification step S14, and the measurement step S16.

The user input signal acquisition function corresponds to the input reception unit 50, the freeze command input signal acquisition determination step S18, and the still image storage determination step S24. The selection function corresponds to the image selection unit 48, the display image selection step S20, and the display image selection step S21.

The program may include an image quality evaluation function corresponding to the image quality evaluation unit 42D and the image quality evaluation step S17.

A program for causing a computer to implement the above-described image processing function can be stored in a computer-readable information storage medium, which is a non-transitory information storage medium that is a tangible object, and the program can be provided through the information storage medium.

In addition, instead of the aspect in which the program is stored and provided in the non-transitory information storage medium, an aspect in which a program signal is provided via a communication network is also possible.

Regarding to Combination of Embodiment and Modification Example

The components described in the above-described embodiment and the components described in the modification examples can be appropriately combined and used, and some of the components can be replaced.

In the above-described embodiments of the present invention, the components can be appropriately changed, added, or deleted without departing from the scope of the present invention. The present invention is not limited to the embodiments described above, and many modifications can be made by those having ordinary knowledge in the art within the technical spirit of the present invention.

EXPLANATION OF REFERENCES

10: endoscope system
14: medical image processing device
14A: medical image processing device
38: endoscopic image
38A: moving image
38B: frame image
$38B_1$: frame image
$38B_2$: frame image
$38B_3$: frame image
$38B_4$: frame image
$38B_5$: frame image
$38B_6$: frame image
$38B_7$: frame image
39: still image
40: image acquisition unit
42: image recognition unit
42A: region of interest detection unit
42B: classification unit
42C: measurement unit
42D: image quality evaluation unit
43: image recognition unit
44: display control unit
46: storage unit
46A: endoscopic image storage unit
46B: region of interest storage unit
46C: classification result storage unit
46D: measurement result storage unit
46E: selected image storage unit
46F: image quality storage unit
47: storage unit
48: image selection unit
49: operation unit
50: input reception unit
100: endoscope main body
102: hand operation portion
104: insertion portion
106: universal cable
108: light guide connector
112: flexible portion
114: bendable portion
116: distal end rigid portion
116A: distal-side end surface
123: illumination portion
123A: illuminating lens
123B: illuminating lens
126: forceps port
130: imaging portion
132: imaging lens
134: imaging element
136: drive circuit
138: analog front end
141: air supply and water supply button
142: suction button
143: function button
144: imaging button
170: light guide
200: processor device
202: image input controller
204: image processing unit
205: communication control unit
206: video output unit
207: storage unit
208: operation unit
209: voice processing unit
209A: speaker
210: CPU
211: ROM
212: RAM
300: light source device
310: light source
310B: blue light source
310G: green light source
310R: red light source
330: stop
340: condensing lens
350: light source control unit
400: monitor
500: region of interest
502: bounding box
504: classification result
506: measurement result
508: arrow line
S10 to S28: each step of medical image processing method

What is claimed is:

1. A medical image processing device comprising:
a processor configured to acquire medical images; and
a storage device configured to store the medical images; wherein
the processor performs recognition processing on the acquired medical images to obtain a recognition result related to a region of interest;
compares the recognition result of each of the medical images acquired with the recognition result of the medical image previously stored in the storage device and updates the medical image to be selected on the basis of a comparison result of the recognition results;
acquires a user input signal transmitted according to an operation of a user for performing a freeze display or a still image storage;
in a case where the user input signal is acquired, selects a medical image acquired at a timing near a timing at which the user input signal is acquired from the updated medical images for which the recognition result related to the region of interest detected in the medical images has been obtained in the recognition processing;

displays, on a monitor, the selected medical image and an emphasis display to emphasize the region of interest detected in the selected medical image as the recognition result related to the region of interest detected in the selected medical image; and stores emphasis display information in association with the region of interest, the emphasis display information including a position of the emphasis display and a size of the emphasis display.

2. The medical image processing device according to claim 1, wherein
the processor displays, on the monitor, the selected medical image for a certain period from the timing at which the user input signal is acquired.

3. The medical image processing device according to claim 2, wherein
the processor performs processing on the selected medical image according to the recognition result of the selected medical image, and
displays, on the monitor, the selected medical image on which the processing is performed.

4. The medical image processing device according to claim 1, wherein
the storage device stores the selected medical image.

5. The medical image processing device according to claim 4,
wherein the storage device stores the selected medical image in association with the recognition result of the selected medical image.

6. The medical image processing device according to claim 4, wherein
the processor performs processing on the selected medical image according to the recognition result of the selected medical image, and
wherein the storage device stores the selected medical image on which the processing is performed.

7. The medical image processing device according to claim 1, wherein
the processor evaluates an image quality of the acquired medical images, and
selects the selected medical image according to an image quality evaluation result of the selected medical image.

8. The medical image processing device according to claim 7,
wherein the processor evaluates at least one of blurriness, shake, brightness, presence or absence of noise, or sharpness of the medical images to be evaluated.

9. The medical image processing device according to claim 1,
wherein the processor selects the selected medical image on the basis of a period between the timing at which the user input signal is acquired and the timing at which the selected medical image is acquired.

10. The medical image processing device according to claim 1,
wherein the processor classifies the acquired medical images into one or more prescribed classes, and
selects the selected medical image classified into a predetermined class.

11. The medical image processing device according to claim 1,
wherein the processor measures the acquired medical images, and
selects the selected medical image in which a value measured is equal to or more than a predetermined threshold value.

12. The medical image processing device according to claim 1,
wherein the storage device stores the medical images acquired in a prescribed period.

13. The medical image processing device according to claim 1, wherein
the processor applies emphasis processing on the region of interest;
selects the selected medical image in which the region of interest has been applied with the emphasis processing as the selected medical image for which the recognition result related to the region of interest has been obtained; and
displays, on the monitor, the emphasis display emphasizing the region of interest as the recognition result related to the region of interest.

14. The medical image processing device according to claim 13, wherein
the processor specifies a position of the region of interest;
defines the position of the emphasis display according to the position of the region of interest;
specifies a size of the region of interest; and
defines the size of the emphasis display according to the size of the region of interest.

15. The medical image processing device according to claim 13, wherein the processor stores different emphasis in association with the region of interest, the different emphasis being different from the emphasis applied for displaying the selected medical image.

16. A processor device comprising:
a processor configured to control an endoscope, and acquire medical images; and
a storage device configured to store the medical images acquired; wherein
the processor performs recognition processing on the acquired medical images to obtain a recognition result related to a region of interest;
compares the recognition result of each of the medical images acquired with the recognition result of the medical image previously stored in the storage device and updates the medical image to be selected on the basis of a comparison result of the recognition results;
acquires a user input signal transmitted according to an operation of a user for performing a freeze display or a still image storage;
in a case where the user input signal is acquired, selects a medical image acquired at a timing near a timing at which the user input signal is acquired from the updated medical images for which the recognition result related to the region of interest detected in the medical images has been obtained in the recognition processing;
displays, on a monitor, the selected medical image and an emphasis display to emphasize the region of interest detected in the selected medical image as the recognition result related to the region of interest detected in the selected medical image; and
stores emphasis display information in association with the region of interest, the emphasis display information including a position of the emphasis display and a size of the emphasis display.

17. An endoscope system comprising:
an endoscope;

a medical image processing device that performs processing on an endoscopic image acquired by using the endoscope,
wherein the medical image processing device includes
a processor configured to control the endoscope, and acquire medical images; and
a storage device configured to store the medical images acquired; wherein
the processor performs recognition processing on the acquired medical images to obtain a recognition result related to a region of interest;
compares the recognition result of each of the medical images acquired with the recognition result of the medical image previously stored in the storage device and updates the medical image to be selected on the basis of a comparison result of the recognition results;
acquires a user input signal transmitted according to an operation of a user for performing a freeze display or a still image storage;
in a case where the user input signal is acquired, selects a medical image acquired at a timing near a timing at which the user input signal is acquired from the updated medical images for which the recognition result related to the region of interest detected in the medical images has been obtained in the recognition processing;
displays, on a monitor, the selected medical image and an emphasis display to emphasize the region of interest detected in the selected medical image as the recognition result related to the region of interest detected in the selected medical image; and
stores emphasis display information in association with the region of interest, the emphasis display information including a position of the emphasis display and a size of the emphasis display.

18. A medical image processing method comprising:
acquiring medical images;
storing the acquired medical images;
performing recognition processing on the acquired medical images to obtain a recognition result related to a region of interest;
comparing the recognition result of each of the medical images acquired with the recognition result of the medical image previously stored in the storage device and updating the medical image to be selected on the basis of a comparison result of the recognition results;
acquiring a user input signal transmitted according to an operation of a user for performing a freeze display or a still image storage;
in a case where the user input signal is acquired, selecting a medical image acquired at a timing near a timing at which the user input signal is acquired from the updated medical images for which the recognition result related to the region of interest detected in the medical images has been obtained in the recognition processing;
displaying, on a monitor, the selected medical image and an emphasis display to emphasize the region of interest detected in the selected medical image as the recognition result related to the region of interest detected in the selected medical image; and
storing emphasis display information in association with the region of interest, the emphasis display information including a position of the emphasis display and a size of the emphasis display.

19. A non-transitory, tangible computer-readable medium having a program stored thereon, the program for causing a computer to implement:
an image acquisition function of acquiring medical images;
an acquired image storage function of storing the acquired medical images;
a recognition processing function of performing recognition processing on the acquired medical images to obtain a recognition result related to a region of interest;
a function of comparing the recognition result of each of the medical images acquired with the recognition result of the medical image previously stored in the storage device and updating the medical image to be selected on the basis of a comparison result of the recognition results;
a user input signal acquisition function of acquiring a user input signal transmitted according to an operation of a user for performing a freeze display or a still image storage;
a selection function of, in a case where the user input signal is acquired, selecting a medical image acquired at a timing near a timing at which the user input signal is acquired from the updated medical images for which the recognition result related to the region of interest detected in the medical images has been obtained in the recognition processing;
a display function of displaying, on a monitor, the selected medical image and an emphasis display to emphasize the region of interest detected in the selected medical image as the recognition result related to the region of interest detected in the selected medical image; and
a storage function of storing emphasis display information in association with the region of interest, the emphasis display information including a position of the emphasis display and a size of the emphasis display.

* * * * *